United States Patent [19]
Fosslien

[11] 4,311,484
[45] Jan. 19, 1982

[54] SPECIMEN SAMPLING APPARATUS

[75] Inventor: Egil Fosslien, Glenview, Ill.

[73] Assignee: Cortex Research Corporation, Northbrook, Ill.

[21] Appl. No.: 138,550

[22] Filed: Apr. 9, 1980

[51] Int. Cl.³ .................. G01N 1/14; G01N 33/48; G01N 35/06

[52] U.S. Cl. .................. 73/864.21; 23/230 R; 23/230 B; 73/864.24; 422/63; 422/65; 422/100; 422/103

[58] Field of Search .............. 422/103, 100, 65, 63; 23/230 R, 230 B; 73/425.6

[56] References Cited

U.S. PATENT DOCUMENTS

| | | | |
|---|---|---|---|
| 3,607,097 | 9/1971 | Auphan et al. | 422/65 |
| 3,676,679 | 7/1972 | Waters . | |
| 3,935,073 | 1/1976 | Waters . | |
| 4,120,662 | 10/1978 | Fosslien | 422/100 |

OTHER PUBLICATIONS

Bactec Flyer.

*Primary Examiner*—Ronald Serwin
*Attorney, Agent, or Firm*—Senniger, Powers, Leavitt and Roedel

[57] ABSTRACT

Method of and apparatus for obtaining a sample from a specimen of blood or the like in a closed container at a first pressure and for delivering the sample to an analyzer for analysis. The apparatus comprises a hollow needle for penetrating the closed container movable from a retracted position to an extended position in which it penetrates the container for drawing a specimen sample therefrom, and back to its retracted position. A conduit connects the needle and the analyzer for delivery of a specimen sample to the latter. An aspirator reduces the pressure in this conduit to a pressure less than the aforesaid first pressure when the needle is in its extended position, a specimen sample thereby being aspirated from the container into the conduit for delivery to the analyzer. The apparatus is responsive to this aspiration to initiate transfer of the specimen sample from the conduit into the analyzer. The pressure in the conduit is at least equal to the first pressure following aspiration, thereby enabling the specimen sample readily to be drawn into the analyzer.

43 Claims, 47 Drawing Figures

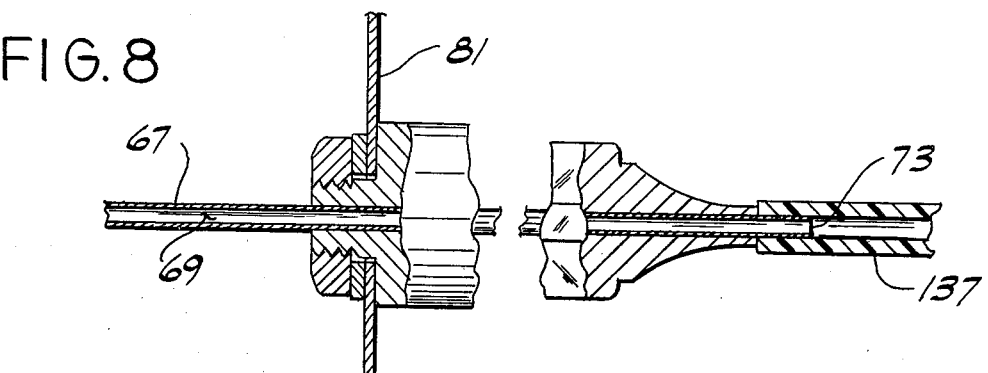
FIG. 8
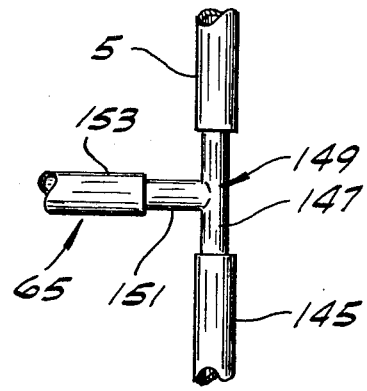
FIG. 15A
FIG. 10
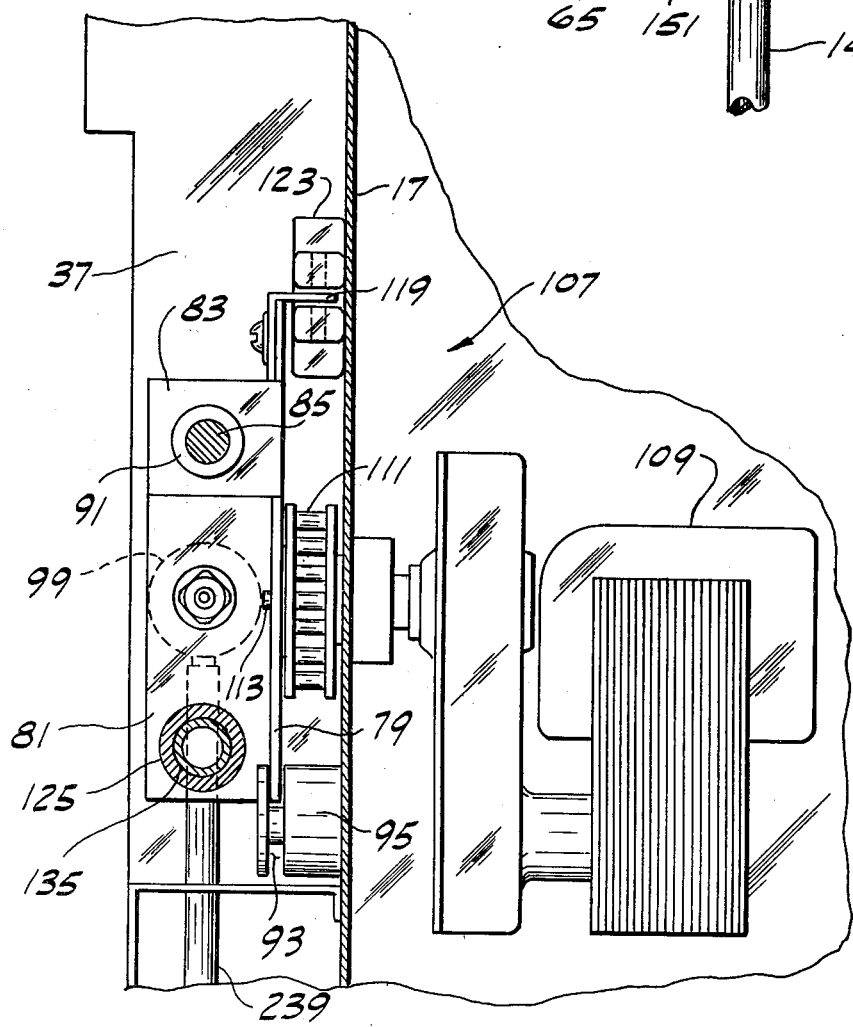

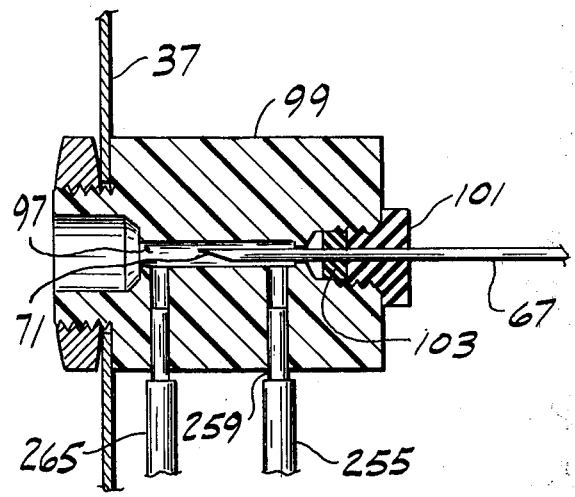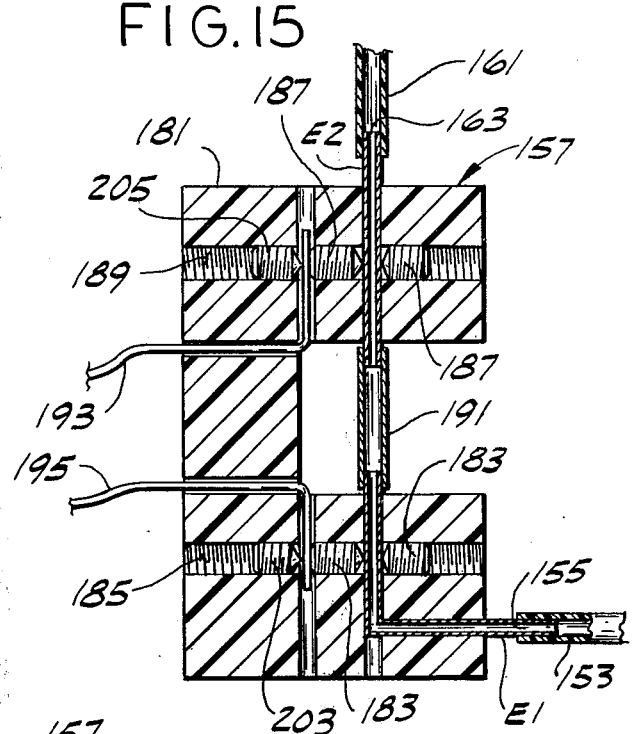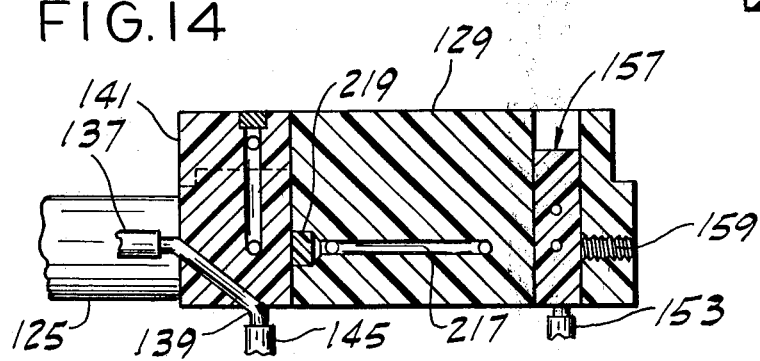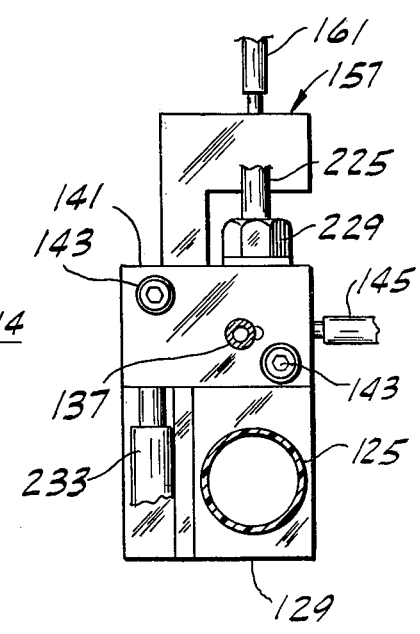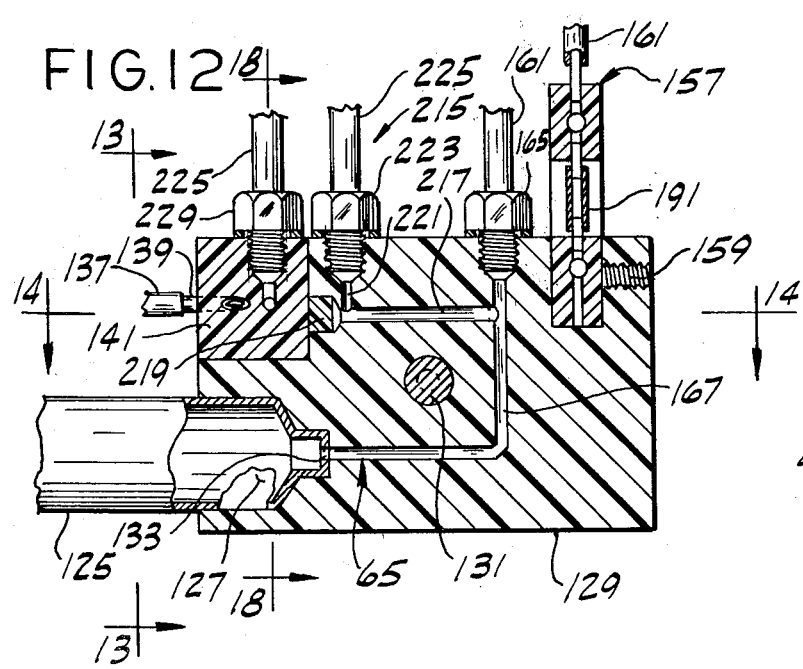

FIG.16
FIG.17
FIG.18
FIG.20
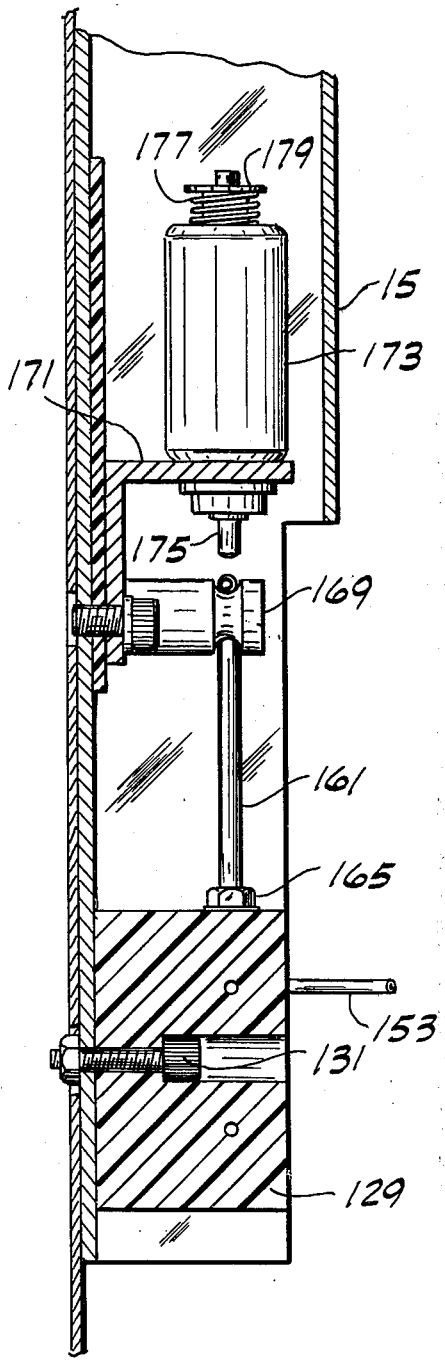
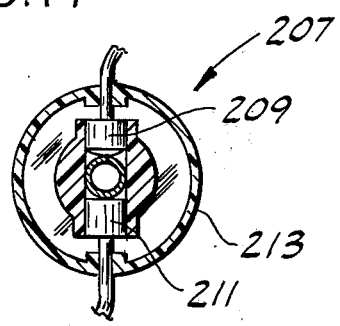
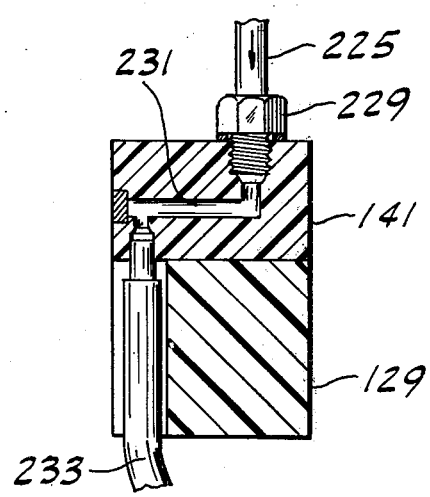
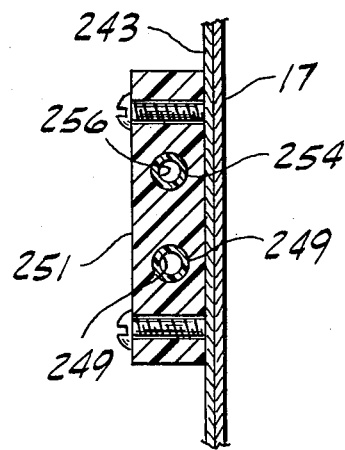

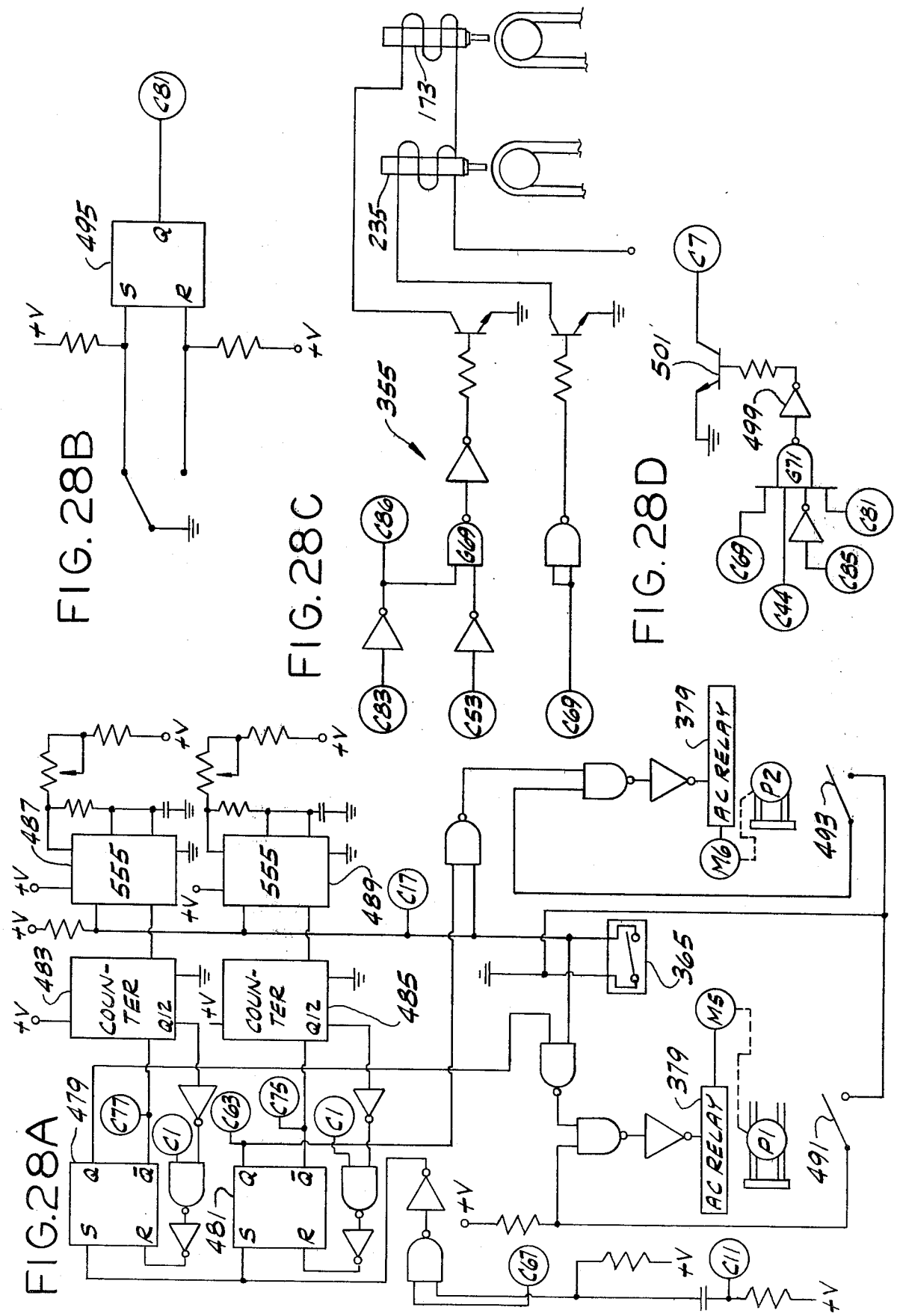

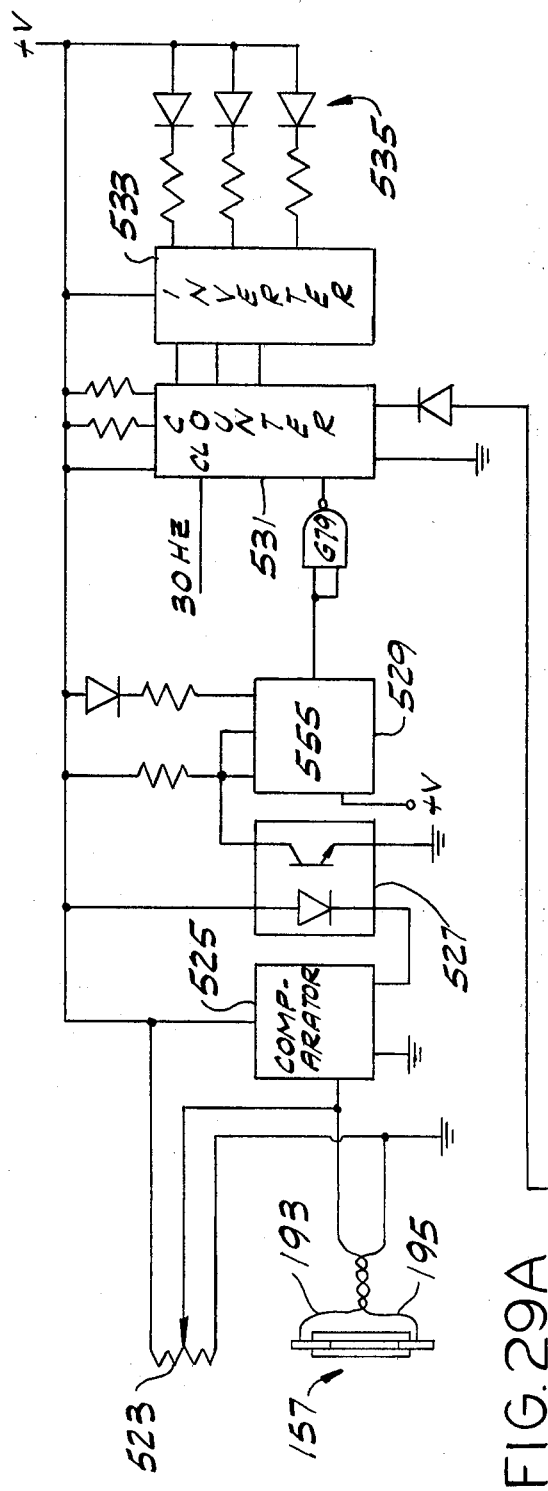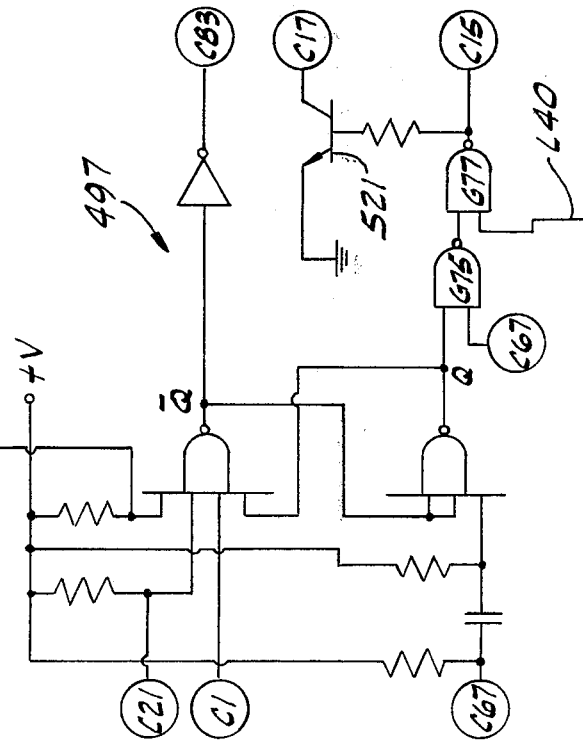
FIG.29A

SPECIMEN SAMPLING APPARATUS

BACKGROUND OF THE INVENTION

This invention relates to sampling apparatus and more particularly to apparatus for obtaining a sample from a specimen of blood or the like and for delivering the sample to means for analyzing it, such as the blood cell counter sold under the trademark "Coulter Counter" Model S by Coulter Electronics, Inc. of Hialeah, Florida, which is used in hospital and commercial laboratories to conduct various tests on whole blood.

Preparatory to analysis, a sample of whole blood is drawn from a patient and typically stored under negative pressure (i.e., a pressure less than atmospheric) in a glass tube with a rubber stopper, such as the type sold under the trade designation "Vacutainer" by Becton-Dickenson and Company of East Rutherford, New Jersey. The blood in this tube is gently and carefully mixed to obtain an even distribution of blood cells and then a sample of the blood is withdrawn for analysis. Heretofore, this has been accomplished in various ways, such as by means of separate mixing and sampling devices or by a device as described in my U.S. Pat. No. 4,120,662.

The specimen sampling apparatus described in this U.S. patent mixes the contents of a series of specimen tubes and delivers them sequentially to a sampling station where a needle, which is connected via a conduit to the intake of a suitable analyzer such as a "Coulter Counter", penetrates the rubber stopper for aspiration of a specimen sample from the tube into the needle and thence through the conduit to the analyzer. However, inasmuch as the contents of the tube are typically under a negative pressure, aspiration of a specimen sample from the tube has presented a problem in that certain analyzers, such as the "Coulter Counter", are unable without modification to develop a negative pressure sufficient to draw a sample from the tube. This problem could be overcome by making major modifications to the analyzer but this would be expensive and complicated.

The contamination of one specimen with particles or cells from another has also presented a problem in prior art sampling apparatus. For sampling apparatus generally in the field of this invention, reference may be made to U.S. Pat. Nos. 3,935,073 and 3,676,679.

SUMMARY OF THE INVENTION

Among the several objects of this invention may be noted the provision of an improved method of and apparatus for obtaining samples from specimens of blood or the like contained in a series of closed containers under negative pressure, and for delivering said samples to suitable analyzing means at a greater pressure, such as atmospheric pressure, thereby enabling ready aspiration of the samples into the analyzing means; the provision of such apparatus in which an operator is not exposed to health hazards such as possibly infective aerosols from the sample while samples are being withdrawn from the specimen tubes and delivered to the analyzing means; the provision of such apparatus which simplifies the sampling of blood or the like; the provision of such apparatus in which the possibility of contaminating one specimen with particles or cells from another is avoided; the provision of such apparatus wherein a plurality of specimen tubes may be bulk-loaded into the apparatus in a predetermined sequence for separate and sequential delivery to the sampling station of the apparatus; the provision of such apparatus which withdraws only a predetermined quantity of sample blood or the like from a container; the provision of such apparatus which signals an alarm if a predetermined quantity of sample blood or the like is not withdrawn from the container within a predetermined time interval; and the provision of such apparatus which is reliable, economical to use, easy to install and operate, and requires little maintenance.

Generally, apparatus of the present invention is useful for obtaining a sample from a specimen of blood or the like in a closed container at a first pressure less than atmospheric pressure and for delivering the sample to an analyzer for analysis, the analyzer having intake means for intake of the specimen sample into it. The apparatus comprises means for penetrating the closed container, the penetrating means having a passage therein with an inlet for entry of a specimen sample into the passage and an outlet for exit of the sample from the passage. The penetrating means is movable from a retracted position to an extended position in which it penetrates the closed container with its inlet in position for entry of a specimen sample into the passage, and back to its retracted position. Conduit means connects the outlet of the passage with the intake means of the analyzer for delivery of a specimen sample to the latter. The apparatus further comprises means for reducing the pressure in the conduit means to a pressure less than the aforesaid first pressure when the penetrating means is in its extended position thereby to aspirate a specimen sample from the container into the passage and the conduit means for delivery to the intake means of the analyzer. Means responsive to this aspiration initiates transfer of the specimen sample from the conduit means into the analyzer. The pressure in the needle passage and conduit means is greater than the first pressure following aspiration, thereby enabling the specimen sample readily to be drawn through the intake means into the analyzer for analysis.

The method of this invention also involves obtaining a sample from a specimen of blood or the like contained in a closed container at a first pressure less than atmospheric pressure and delivering the sample to an analyzer for analysis, the analyzer having intake means for entry of the specimen sample into the analyzer. The method comprises penetrating the closed container with means connected via conduit means to the intake means, the penetrating means having a passage therein with an inlet for entry of a specimen sample into the passage and an outlet for exit of the sample from the passage into the conduit means. The method further comprises reducing the pressure in the passage and the conduit means to a pressure less than the aforesaid first pressure thereby to aspirate a specimen sample from the container into the passage and conduit means for delivery to the intake means of the analyzer. The penetrating means is withdrawn from the container following aspiration with the pressure in the aforementioned conduit means then being at least equal to said first pressure. Transfer of specimen sample from the conduit means ino the analyzer is then initiated.

Other objects and features will be in part apparent and in part pointed out hereinafter.

BRIEF DESCRIPTION OF THE DRAWINGS

FIG. 8 is an enlarged view of a portion of the penetrating means shown in FIG. 7 with parts broken away to illustrate details;

FIG. 9 is an enlarged portion of FIG. 7 showing a rinse chamber for the penetrating means;

FIG. 10 is a vertical section on line 10—10 of FIG. 6;

FIG. 12 is an enlarged portion of FIG. 11 showing, among other things, a main valve block and associated parts, portions being broken away and portions being shown in section to illustrate details;

FIG. 13 is a vertical section on line 13—13 of FIG. 12;

FIG. 14 is a horizontal section on line 14—14 of FIG. 12;

FIG. 15 is an enlarged vertical section on line 15—15 of FIG. 11;

FIG. 15A is an enlarged portion of FIG. 1 showing a connection between the specimen sampling apparatus and the analyzer;

FIG. 16 is a vertical section on line 16—16 of FIG. 11;

FIG. 17 is an enlarged vertical section on line 17—17 of FIG. 11;

FIG. 18 is a vertical section on line 18—18 of FIG. 12;

FIG. 20 is a vertical section on line 20—20 of FIG. 19;

FIGS. 28A–E are schematic diagrams of pump and valve control circuitry used in the apparatus of the present invention; and FIGS. 29A and 29B are schematic diagrams of certain additional sensor and logic circuitry used in the apparatus of the present invention.

Corresponding reference characters indicate corresponding parts throughout the several views of the drawings.

DESCRIPTION OF THE PREFERRED EMBODIMENT

Figure 1:
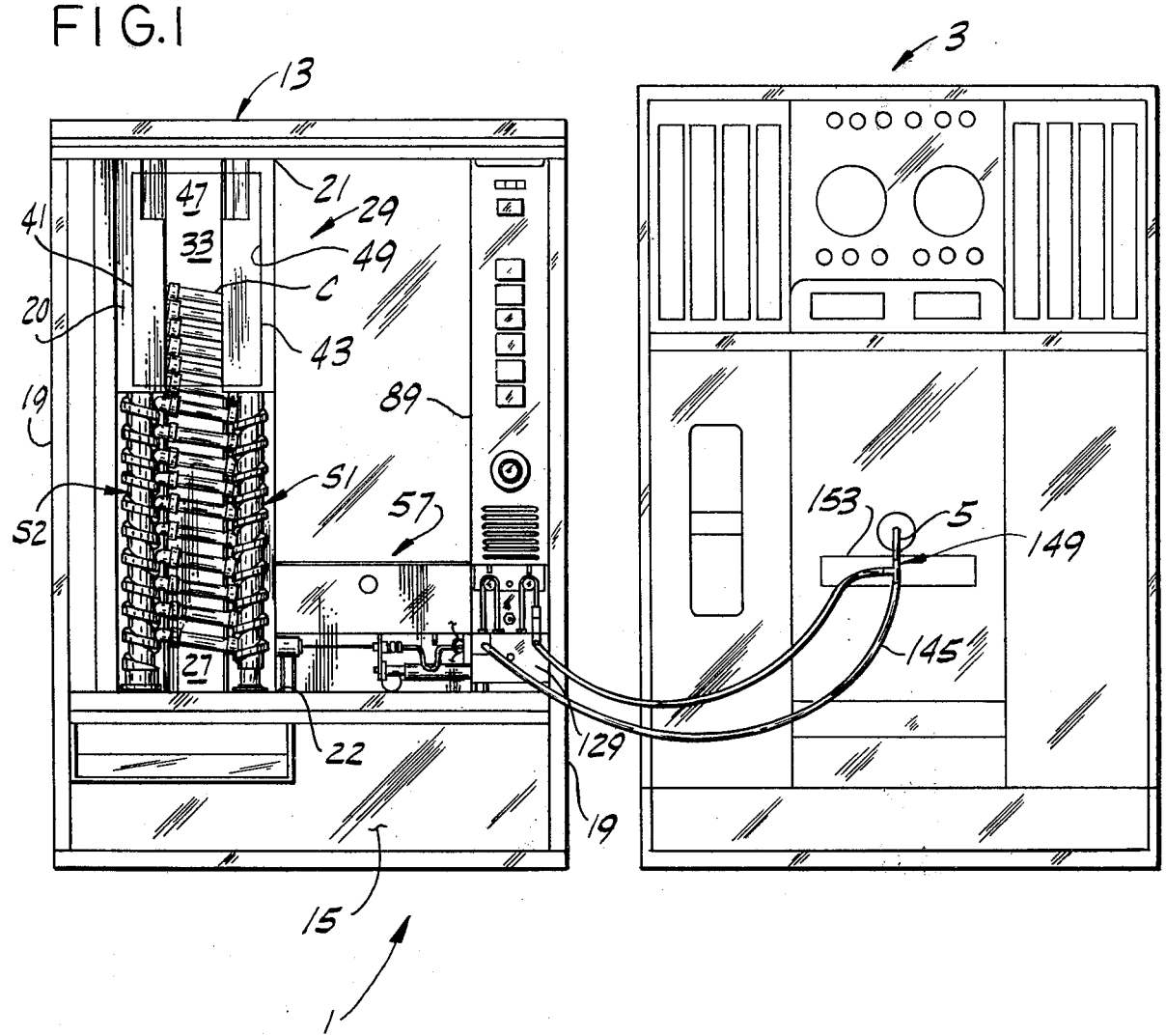
FIG. 1 is a front elevational view in which apparatus of the present invention for obtaining a sample of blood or the like from a closed container is shown on the left, and an analyzer for analyzing the sample is shown on the right.

Referring now to the drawings, particularly to FIG. 1, sampling apparatus of the present invention is indicated in its entirety at 1 and represents an improvement upon the apparatus described in my U.S. above-mentioned U.S. Pat. No. 4,120,662. Apparatus 1 is operable to obtain a sample of blood, for example, in a closed container C at a pressure less than atmospheric pressure and to deliver it to an analyzer 3 at a pressure equal to or greater than atmospheric pressure. This enables the analyzer, which may be a "Coulter" Model S cell counter having intake means constituted by an intake line 5, more readily to aspirate the specimen sample through intake line 5 and into the analyzer for analysis. As noted above in this regard, the "Coulter Counter" is capable of developing or generating a negative pressure less than atmospheric. However, this negative pressure may not be substantially less than the negative pressure in a closed container C, making aspiration of a sample from the container by the analyzer difficult if not impossible. Thus the fact that apparatus 1 is able to deliver a sample from such a container C to intake line 5 at a pressure at least equal to atmospheric permits quick and easy aspiration of the sample by the analyzer into intake line 5.

Apparatus 1 is adapted for handling a series of closed containers C, each of which comprises an elongate tubular body or tube 7 (see FIG. 2) closed at one end and having its other end stopped with a rubber plug 9 having a diameter greater than that of the tube. Adaptor means comprising a circular sleeve 11 removably fitted around the tube and spaced longitudinally of the tube from the plug is provided for increasing the effective diameter of the tube to that of the plug. This is important for reasons which will become apparent hereinafter. While sleeve 11 is preferably removable from tube 7 it will be understood that it may be integrally formed with the tube.

Apparatus 1 comprises a cabinet 13 having front, back and side walls designated 15, 17 (see FIG. 3) and 19, respectively. A pair of substantially parallel vertical shafts S1 and S2 are mounted for rotation within cabinet 13 behind a transparent door 20 (see FIG. 3) which is hinged at 21 and 22 for swinging open and closed. Shafts S1 and S2 have upper and lower sections 23, 25, the latter of which are screw-threaded and constitute means for conveying a series of closed containers C downwardly and generally in horizontal position to a sampling station 27, and for imparting a gentle rocking and rotating motion to the containers as they are being so conveyed thereby to obtain a substantially uniform mix or distribution of particles (e.g., blood cells) contained therein. The lower screw-threaded shaft sections 25 of shafts S1 and S2 are similar in construction and operation to feed screws S1 and S2 in my above-mentioned U.S. Pat. No. 4,120,662 and reference may be made to that patent for further details.

Figure 3:
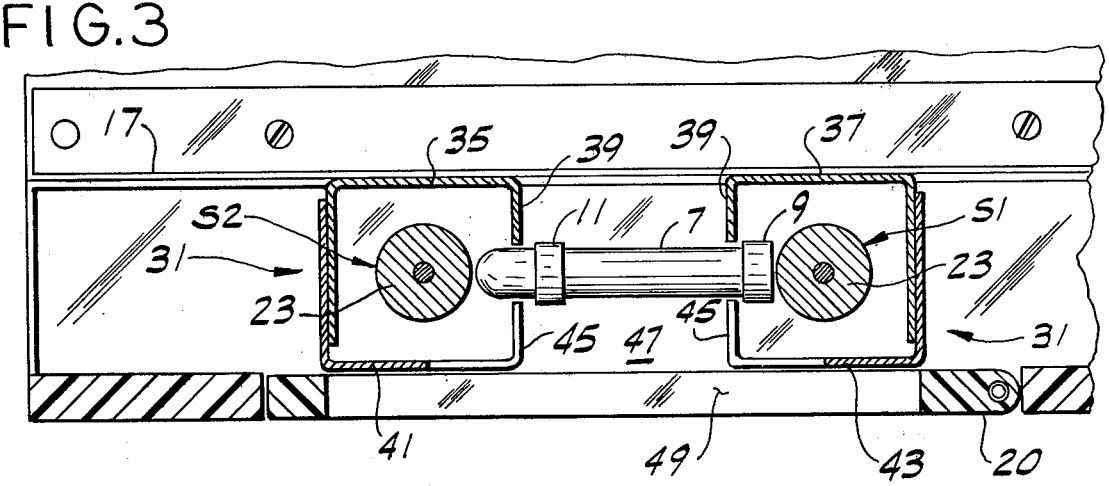
FIG. 3 is an enlarged horizontal section on line 3—3 of FIG. 2.
Figure 4:
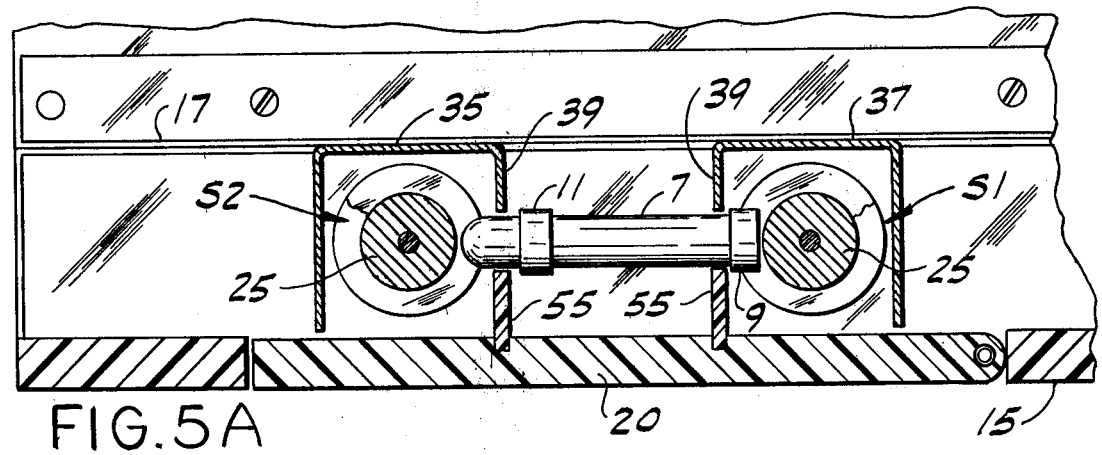
FIG. 4 is an enlarged horizontal section on line 4—4 of FIG. 2.

In accordance with this invention, means generally designated 29 is provided for feeding a plurality of containers C one after another in a predetermined sequence to the upper ends of screw-threaded sections 25 of shafts S1 and S2 for conveyance to sampling station 27. More specifically, means 29 comprises the upper thread-free sections 23 of shafts S1 and S2, and means 31 on opposite sides of (i.e., forward and rearward of) the upper shaft sections for retaining a series of containers C stacked one atop another in generally horizontal position between the shafts (FIG. 3). The upper shaft sections 23 and retaining means 31 together define a vertical guideway 33 through which a plurality of containers C are fed to the upper ends of screw shaft sections 25.

More particularly, retaining means 31 comprises a pair of rear guide rails 35, 37 secured in vertical position to the back wall of the cabinet. These rails, which extend the entire length of shafts S1 and S2, are generally J-shaped in cross section and have parallel lips 39 projecting forwardly from the back wall of the cabinet between shafts S1 and S2. A second pair of guide rails 41, 43 are disposed forwardly of upper shaft sections 23 and are secured (e.g., welded) to rear guide rails 35, 37 as shown in FIG. 3. The forward guide rails 41, 43 are shorter than the rear guide rails, extending only the length of the upper shaft sections 23 rather than the entire length of shafts S1 and S2, but are identical in cross-sectional shape to the rear guide rails, having parallel lips 45 extending rearwardly between upper shaft sections 13. The vertical edges of lips 39 of the rear rails and the vertical edges of lips 45 of the forward rails are disposed generally opposite one another and spaced apart a distance somewhat greater than the diameter of the tube 7. The lateral spacing between the lips 39 of the rear guide rails and the lateral spacing between the lips 45 of the forward guide rails is less than the length of a container C.

Figure 2:
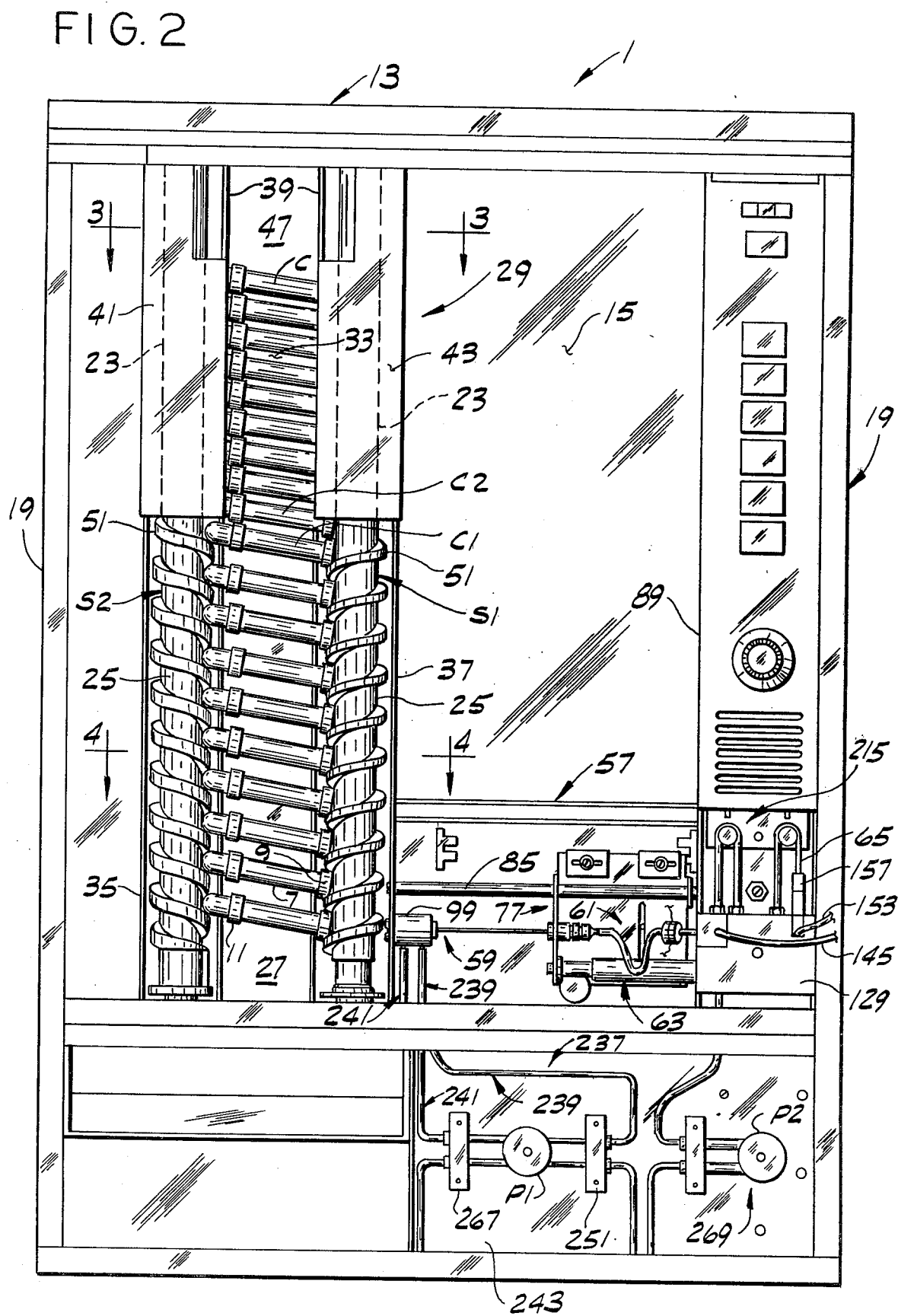
FIG. 2 is an enlarged front elevation of the specimen sampling apparatus with portions removed to illustrate details.

As shown in FIG. 2, the upper portions of forward rails 41, 43 are notched to provide an inlet 47 through which a plurality of containers C may be bulk-loaded into the guideway 33 for delivery to the screw-threaded shaft sections 25. An opening 49 in door 21 provides access to inlet 47 when the door is closed. The bottom of guideway 33 is open, constituting an outlet, and is disposed such that the lowermost container C1 in the guideway rests atop the upper threads 51 of screw shaft sections 25, with the plug of container C1 engaging the upper thread 51 of the right screw shaft section and the end of tube 7 opposite the plug engaging the upper thread 51 of the left screw shaft section. The plug and sleeve of container C2 above C1 are engageable with the plug and sleeve of C1 for maintaining the two tubes generally parallel. The remaining containers C in guideway 33 are also maintained generally parallel in the same fashion.

As more fully described in my U.S. Pat. No. 4,120,662, shaft S1 is operable to rotate in one direction and then the other direction a predetermined number of times while shaft S2 remains stationary, causing the stoppered right ends of the container C between screw shafts 25 to rock up and down and rotate to effect mixing of the blood in the containers. The containers C in guideway 33 are also subjected to this mixing action since they are stacked atop the lowermost container C1 in the guideway which rests directly on the upper threads 51 of the screw shaft sections 25. This is important in that it enables the screw shaft sections to be relatively short in overall length since the contents of the containers are at least partially mixed before they are removed from guideway for conveyance to the sampling station.

Containers C are maintained in engagement with the threads of screw shaft sections 25 by the lips 39 of rear guide rails 35, 37 and by a pair of retaining bars 55 mounted on the rear face of door 20. The rearward vertical edges of the retaining bars are spaced forwardly of the vertical edges of lips 39 a distance somewhat greater than the diameter of tubes 7.

Apparatus 1 is equipped with an aspiration and transfer system 57 for aspirating a specimen sample from each container C when it reaches sampling station 27 and for then delivering the sample to the intake line 5 of analyzer 3. This system 57 comprises means 59 for penetrating the puncturable stoppered (right) end of the container C at sampling station 27, conduit means 61 connecting penetrating means 59 and the intake line 5 of the analyzer, and an aspirator 63 constituting means for reducing the pressure in conduit means 61 when the penetrating means has punctured the container C thereby to aspirate a specimen sample from the container for delivery to intake line 5. The aspirator communicates with conduit means 61 via a second conduit means 65. As will appear, the pressure in the first conduit means increases following aspiration of the specimen sample from container C thereby enabling the sample readily to be drawn by the analyzer through intake line 5.

Figure 6:
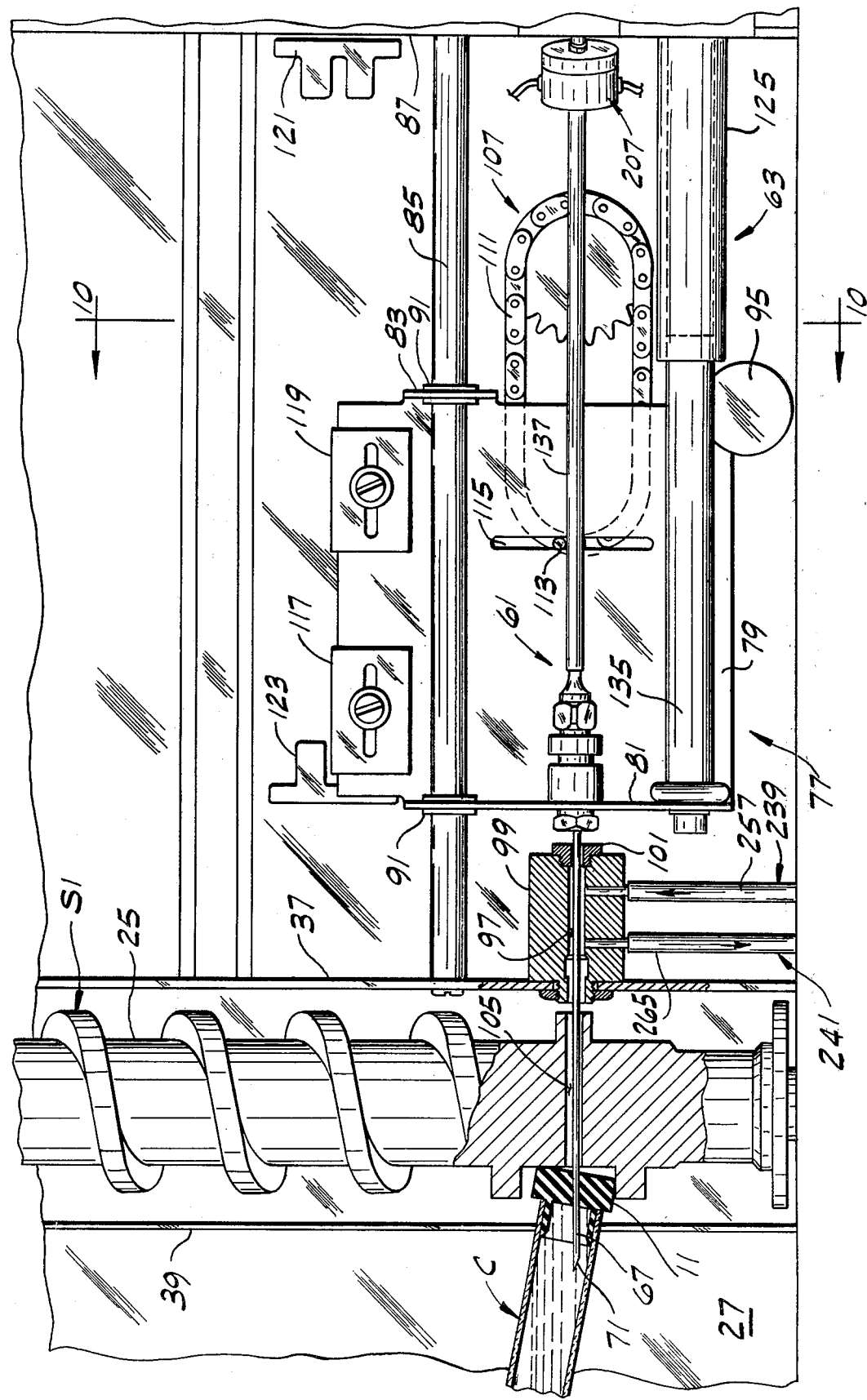
FIG. 6 is an enlarged portion of FIG. 2 showing penetrating means of this invention in an extended position in which it penetrates a container at the sampling station, parts being broken for purposes of illustration.
Figure 7:
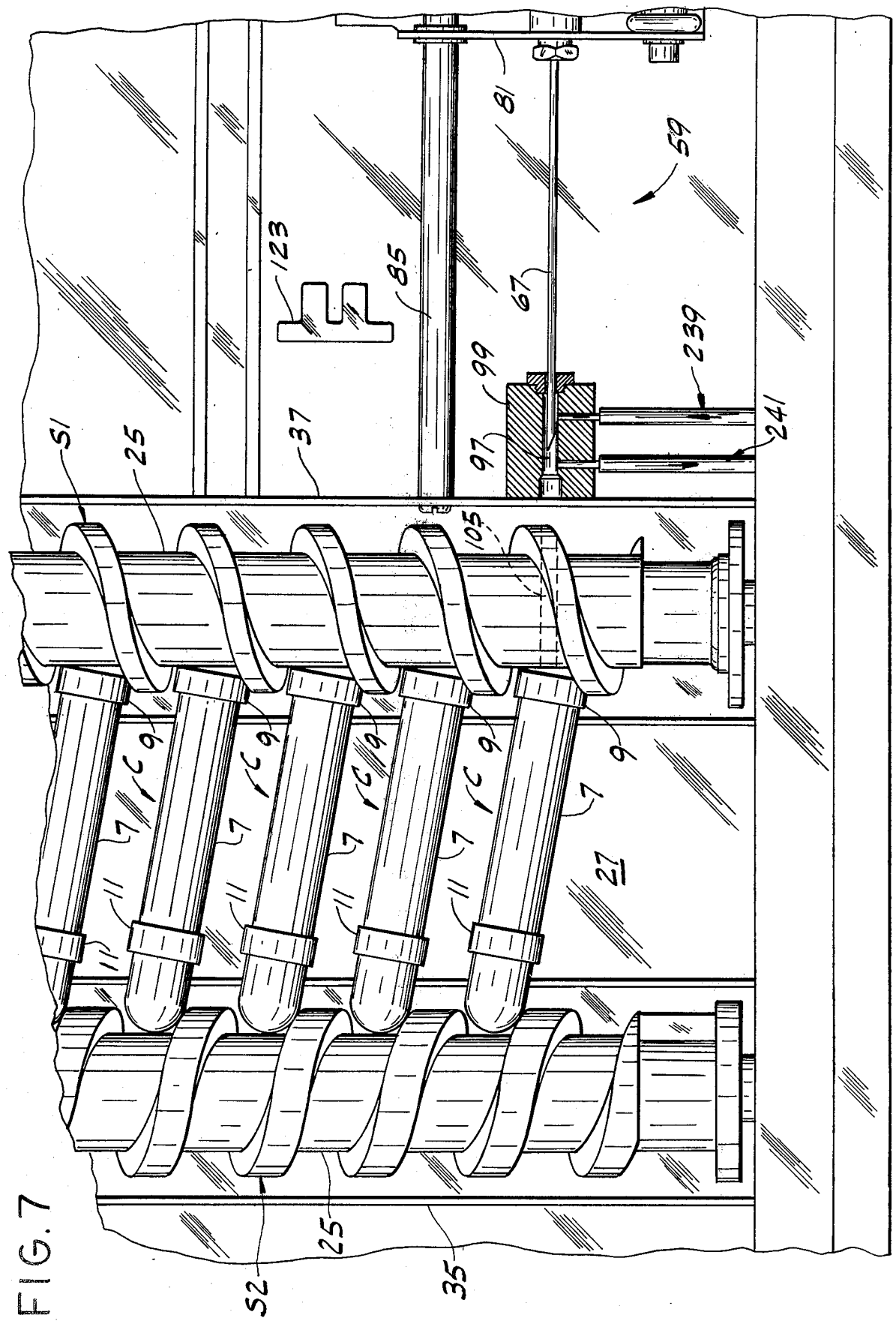
FIG. 7 is a view similar to FIG. 6 with the penetrating means shown in retracted position.

More particularly, penetrating means 59 comprises an elongate horizontally disposed needle 67 having a passage 69 therein (FIG. 8) extending its entire length. The needle is open at its left and right ends to provide an inlet and outlet designated 71 (FIG. 6) and 73 respectively (FIG. 8) for entry of the specimen sample into passage 69 and for exit of the sample therefrom into conduit means 61 which is connected to the outlet end 73 of needle 67. Carriage means indicated generally at 77 is provided for moving the needle from a retracted position (FIGS. 2 and 7) in which the inlet of the needle is exposed to atmosphere, to an extended position (FIG. 6) in which it penetrates the stoppered end of container C at sampling station 27 with inlet 71 in position for entry of specimen sample into the needle passage 69. Means 77 is also operable to move needle 67 back to its retracted position after termination of a predetermined aspiration period (six seconds, for example). Movement of the needle from its retracted to its extended position and then back to its retracted position after aspiration constitutes an aspiration cycle.

Carriage means 77 comprises a carriage in the form of a vertically disposed rectangular carriage plate 79 extending in side-by-side direction with respect to the cabinet and having a pair of forwardly extending vertical flanges at its left and right sides designated 81 and 83, respectively. The carriage is slidable back and forth on a horizontal guide rod 85 extending generally parallel to the back wall of the cabinet between rear guide rail 37 and the left wall 87 of a vertical control post or box 89 at the right side of the cabinet. Suitable bearings 91 mounted in carriage flanges 81, 83 receive guide rod 85 therethrough for facilitating sliding of the carriage on the guide rod. To prevent the carriage from rocking on the guide rod, the lower horizontal edge of the carriage plate 79 is received in an annular groove 93 (see FIG. 10) in a cylindrical guidepost 95 mounted on the back wall 17 of the cabinet.

Needle 67 is suitably mounted on the left carriage flange 81 and extends horizontally and to the left therefrom through a horizontal bore 97 in a needle guide block 99 mounted on rear guide rail 37 (see FIG. 9). The diameter of this bore 97, which is counterbored at its left end, is only slightly larger than the diameter of the needle for reasons which will appear. A nipple 101 threaded into the right end of bore 97 has a hole in it generally coaxial with bore 97 for receiving needle 67 therethrough and guiding it as it moves between its extended and retracted positions. An O-ring 103 in bore 97 at the left end of nipple 101 has a sealing fit with the outer surface of the needle. As will more fully be explained hereinafter, bore 97 in the needle guide block constitutes a rinsing chamber in which the outer surface of the needle is washed as it moves from its extended back to its retracted position and for a brief time thereafter. When in its extended position, the needle extends through a diametrical bore 105 in the threaded screw section 25 of the right shaft S1 and penetrates the puncturable end of the closed container C at the sampling station for aspirating a sepcimen sample therefrom, the sample being aspirated through inlet 71, needle passage 69, outlet 73, and into conduit means 61 for delivery to intake line 5 of the analyzer.

Carriage means 77 further includes drive means 107 for reciprocating the carriage 79 along the guide rod 85 to move the needle between its extended and retracted positions. Drive means 107 comprises an electric motor 109 with a chain-and-sprocket drive 111, and a pin 113 on the chain of the drive receivable in a vertical slot 115 in carriage plate 79. As this pin 113 moves along the oblong path defined by the chain-and-sprocket drive, the carriage and needle are reciprocated between retracted and extended positions. Two L-shaped brackets 117 and 119 are mounted on the carriage adjacent to its upper horizontal edge and extend in a horizontal plane rearwardly from the carriage toward the back wall of the cabinet (FIG. 10). When the carriage is in its fully retracted position, the right bracket 119 interrupts the light beam of a sensor 121 mounted on the back wall of the cabinet adjacent to control post 89, and when the carriage is in its fully extended position the left bracket 117 interrupts the light beam of a sensor 123 mounted on the back wall of the cabinet adjacent guide rail 37. Brackets 117 and 119 are slidably adjustable in the horizontal direction with respect to the carriage.

Aspirator 63, which may be a syringe of the type sold by Hamilton Company of Reno, Nev., comprises a cylindrical barrel 125 mounted in horizontal position with its right end secured in a cylindrical recess 127 (FIGS. 11 and 12) in a relatively large main valve block 129, the latter of which is mounted via a fastener 131 on the back wall of the cabinet at the bottom of the control post 89. The barrel 125 constitutes cylinder means and has an opening 133 at its right end in communication with conduit means 65. A piston 135 is movable axially in the barrel between a retracted (FIG. 11) position in which it is relatively close to the right end of the barrel and an extended (FIG. 6) position in which it is further away from the right end of the barrel. As shown, the piston is mounted on the carriage for movement therewith. Thus, as the carriage slides to the left on guide rod 85 toward its extended position, piston 135 moves from its retracted to its extended position to produce a negative pressure in conduit means 65, and as the carriage slides to the right back toward its retracted position, the piston also moves back to its retracted position.

Conduit means 61 connecting the outlet 73 of needle passage 69 and intake line 5 of the analyzer 3 comprises a line 137 of clear tubing connected at one end (its left end as viewed in FIG. 11) to the right end of needle 67 and at its other (right) end to one end of a rigid connector tube 139 extending obliquely in a horizontal plane through a relatively small secondary valve block 141 received in a notch in the upper left corner of main valve block 129. Secondary valve block 141 is secured to the main valve block by two bolts 143. Conduit means 61 further includes a line 145 (which may also be of clear plastic tubing) connecting the forward end of connector tube 139 to one end of the crosshead 147 of a tee 149, the intake line 5 of analyzer 3 being connected to the other end of the crosshead (FIG. 15A). Second conduit means 65 is connected to the laterally extending leg 151 of tee 149.

Second conduit means 65 extends from tee 149 to the opening 133 at the right end of barrel 125 of the aspirator. It comprises a line 153 of clear flexible tubing extending from leg 151 of the tee to the inlet 155 of sensing means generally designated 157 secured via a fastener 159 in a notch in main valve block 129, a line 161 constituted by a length of clear flexible tubing connecting the outlet 163 of sensing means 157 with a nipple 165 threaded into the upper face of the main valve block, and a passage constituted by a bore 167 in the main valve block 129 extending vertically downwardly in the valve block from nipple 165 and then horizontally to the left to cylindrical recess 127 in which the right end of barrel 125 is received (FIG. 12).

Figure 11:
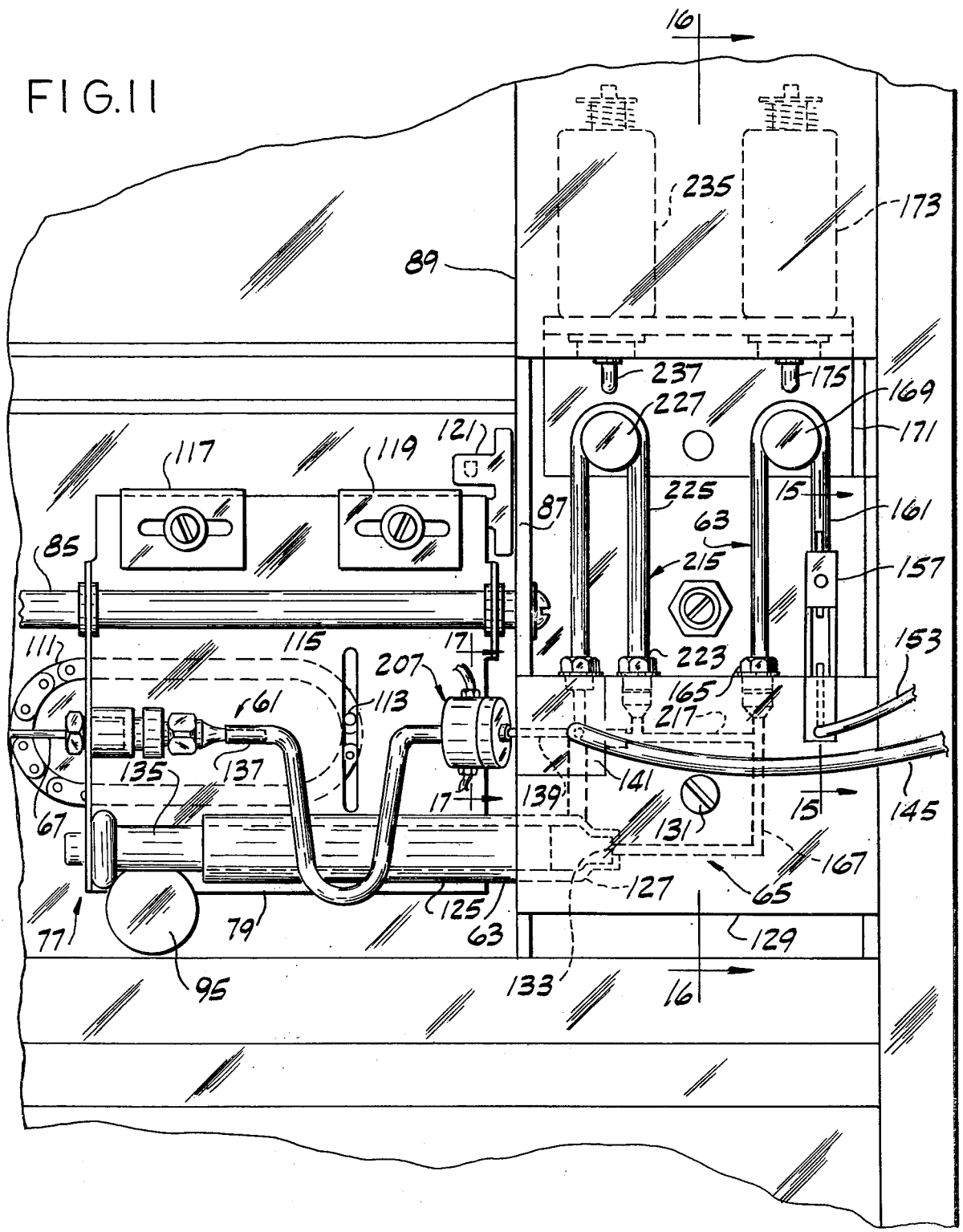
FIG. 11 is an enlarged view of a portion of FIG. 2 with the penetrating means being shown in retracted position.

Line 161 connecting the outlet 163 of sensing means 157 to nipple 165 is trained around a grooved hub 169 mounted on the vertical leg of an L-shaped bracket 171 secured to the back wall of the cabinet (see FIG. 11). Valve means constituted by a solenoid 173 having a plunger 175 is mounted on the horizontal leg of bracket 171 directly above hub 169 and line 161 (FIG. 16). The plunger is biased toward a raised or retracted position by a spring 177 reacting against the top of the solenoid housing against a washer 179 retained on the upper end of the plunger. On energization of the solenoid, plunger 175 is operable to move downwardly against the bias of spring 177 to a lowered or extended position in which it pinches line 161 to close it. As will appear, the solenoid is adapted to close line 161 as the needle 67 and piston 135 are moved by carriage 79 from their retracted to their extended positions, thereby enabling the aspirator to develop a negative pressure in passage 167 and in the portion of line 161 between nipple 165 and plunger 175. Valve 173 is deenergized to open line 161 when the needle reaches its extended position inside container C, thereby reducing the pressure in needle passage 69 and conduit means 61 and 65 to permit aspiration of a specimen sample from the closed container for delivery to intake line 5 of the analyzer.

Sensing means 157 is responsive to the flow of the leading end of an aspirated specimen sample therepast for generating a signal to actuate solenoid valve 173 to close line 161. Means 157 comprises a sensor which is shown in FIG. 15 to comprise a generally C-shaped body 181 of a suitably electrically nonconductive material such as a synthetic resin sold under the trademark "Lucite" by E.I. du Pont De Nemours and Company. The sensor also includes a pair of electrodes E1 and E2 in the form of cylindrical tubes of suitably conductive material such as 18-gauge stainless steel. One electrode, E1, is generally L-shaped and received in horizontal and vertical bores in the lower horizontal leg of the C-shaped body 181. The other electrode E2 is straight and received in a vertical bore through the upper horizontal leg of body 181. Two metal set screws 183 received in a horizontal bore 185 through the sensor body are disposed at opposite sides of electrode E1 and secure the latter in place. Similarly, electrode E2 is held in fixed position by a pair of set screws 187 received in a horizontal bore 189. Line 153 is connected to the lower right end of electrode E1, which constitutes inlet 155, for entry of specimen sample into the sensor, and line 161 is connected to the upper end of electrode E2, which constitutes outlet 163 for exit of specimen sample from the sensor.

A tubular conductivity cell 191 of nonconductive material is positioned between electrodes E1 and E2 and is aligned with respect to the fluid flowpath through the sensor. As shown, the two left screws 183, 187 of the two pairs of set screws securing electrodes E1 and E2 in place are in electrical contact with two wires 193, 195 held in electrical contact with their respective set screws by screws indicated at 203 and 205 in bores 185 and 189, respectively. Thus, when a specimen sample of blood or the like is aspirated from container C through conductivity cell 191, conductivity sensor circuit 201 is completed to send, after a brief time delay (e.g., one second), an electrical signal to solenoid valve 173 to close line 161 and prevent further aspiration. It will be noted that unless the specimen sample is continuous (i.e., uninterrupted) in the conductivity cell 191, the circuit will not be completed, thereby avoiding triggering the solenoid valve if only short slugs of sample are arriving at the sensor. Moreover, the fact that there is a brief time delay between the time the circuit is closed and the time at which the signal is sent to the solenoid valve 173 also ensures that relatively short slugs of specimen samples do not result in the energization of valve 173 and the closing of line 161.

After termination of an aspiration period it is desirable to have means for detecting whether there is sufficient specimen sample in conduit means 61 so that during subsequent aspiration by analyzer 3 air is not drawn through intake line 5 and into the analyzer. An optical sensor 207 positioned as shown in FIG. 11 represents such means. This sensor is mounted around line 137 adjacent the main valve block 129 and is responsive, after termination of the aspiration period, to the absence of specimen sample in line 137 for signalling (e.g., sounding) an alarm. More particularly, sensor 207 comprises an infrared light-emitting diode 209 at one side of line 137 and a phototransistor 211 positioned on the opposite side of the line (see FIG. 17). Both elements 209, 211 are contained in a cylindrical housing 213. If after termination of an aspiration period blood is present in line 137 at the location of the sensor, no alarm is signalled, indicating that there is sufficient specimen sample for aspiration by analyzer 3. However, if there is no blood in line 137 at the sensor (either because of a clot in the line upstream of the sensor or because the trailing end of an insufficient sample is downstream of the sensor), the sensor is adapted to signal an alarm so that the analyzer 3 may be prevented from entering its aspiration mode.

As carriage 79 moves to the right toward its retracted position following aspiration of the specimen sample from the container C at sampling station 27, piston 135 also moves to the right in barrel 125. During this latter movement of the piston, air is expelled through opening 133 in barrel 125 into passage 167 and thence to atmosphere via discharge conduit means generally indicated at 215. The latter comprises a horizontal passage 217 through the main valve block, the right end of this passage communicating with the vertical reach of passage 167 and the left end being plugged as indicated at 219, and a relatively short vertical passage 221 communicating with the horizontal passage 217. The upper end of vertical passage 221 is counterbored and tapped to receive a nipple 223. A flexible discharge line 225 of clear plastic tubing extends upwardly from nipple 223 around a grooved hub 227 mounted on the vertical leg of bracket 171 adjacent hub 169 and then downwardly to another nipple 229 threaded into the top of the secondary valve block 141. A passage 231 (see FIG. 18) through the secondary valve block connects nipple 229 and a line 233 which extends from the outlet end of passage 231 to a suitable waste receptacle (not shown).

A second solenoid valve 235 identical in construction and operation to the above-described solenoid valve 173 for closing line 225 is mounted on the horizontal leg of bracket 171 adjacent solenoid valve 173. The plunger 237 of solenoid valve 235 is disposed directly above discharge line 225 trained around hub 227 and is operable on energization of the solenoid to move downwardly to an extended position to pinch the line 225 against the hub to close it. As will appear, the solenoid is energized to close the discharge line 225 before the carriage 79 and piston 135 thereon move leftwardly from their retracted to their extended positions, thereby enabling a negative pressure to be developed as the piston moves to the left in barrel 125. Solenoid valve 235 is deenergized to open line 225 after termination of an aspiration period and before the carriage and piston move back to their retracted positions, thereby enabling fluid to be expelled from the system via discharge conduit means 215 as the piston moves to the right in the barrel.

Figure 19:
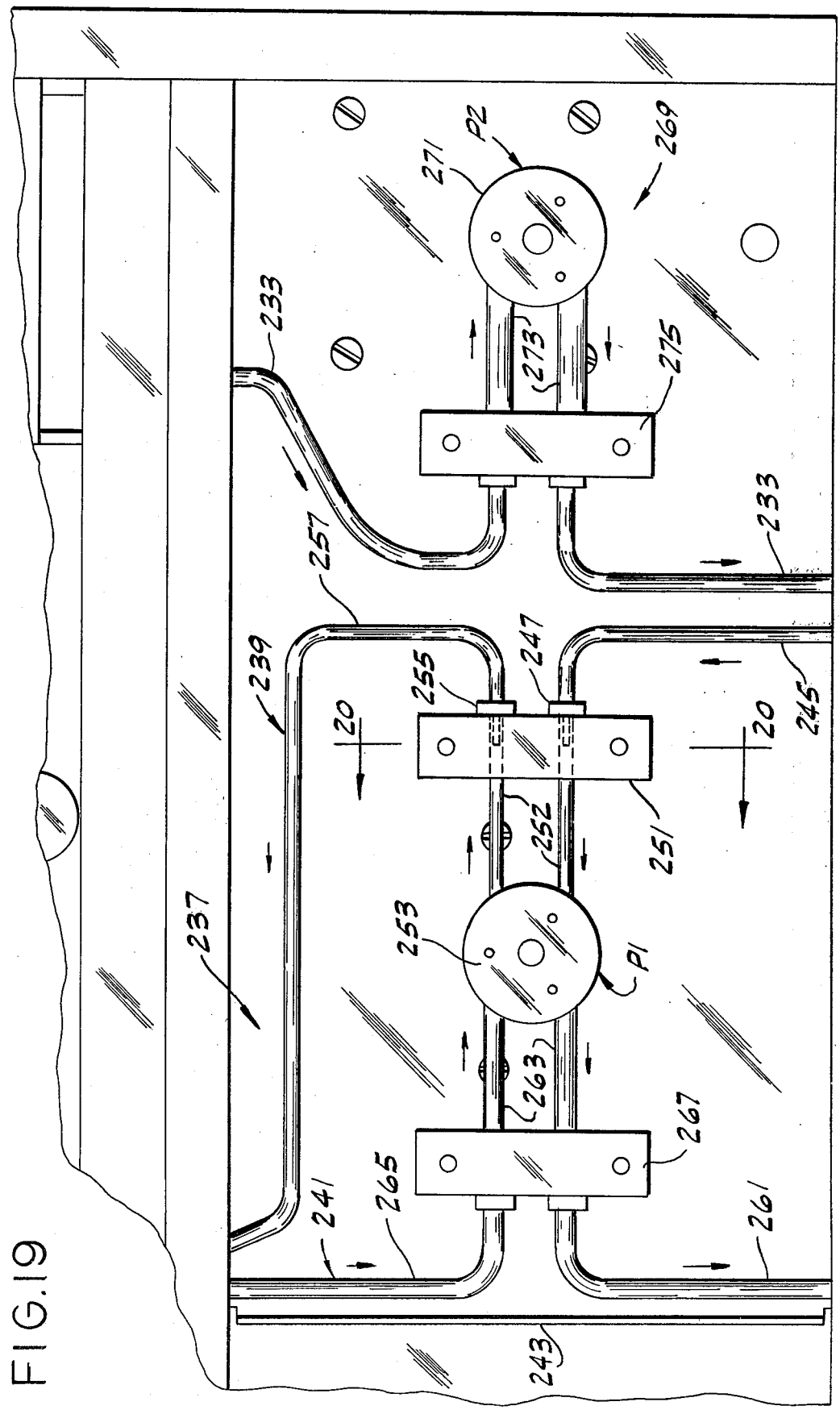
FIG. 19 is an enlarged portion of FIG. 2.

As alluded to above, the aspiration and transfer system of this invention also includes means generally indicated at 237 (see FIGS. 2 and 19) for cleaning the outer surface of the needle as the latter moves from its extended back to its retracted position and for a brief interval thereafter. This is necessary to remove blood or other matter from the needle so that contamination of one specimen with particles or cells from another is avoided. Means 237 comprises the rinsing chamber 97 in the needle guide block 99 described above, a line 239 for supply of a suitable cleaning fluid (such as an 0.85% NaCl solution) to the chamber, a line 241 for drainage of the chamber, and a pump P1 operable to pump cleaning solution through the supply line 239 to the rinse chamber and thence through the drain line 241 to a waste receptacle (not shown). Pump P1 is preferably a peristaltic pump of the type well known in the art and is secured to a mounting plate 243 fastened to the back wall 17 of the cabinet below carriage 79 and the main valve block 129. Supply line 239 comprises three sections, a first section 245 connected at one end to a source (not shown) of cleaning solution and at its other end to a nipple 247 received in one end (the right end as viewed in FIG. 19) of a horizontal bore 249 (FIG. 20) through a retaining bar 251 bolted to mounting plate 243, a second section 252 of resilient material extending around the head 253 of pump P1 and having one end secured to nipple 247 and its other end secured to a nipple 255 in the right end of a second horizontal bore 256 through retaining bar 251, and a third section 257 connected at one end to nipple 255 and at its other end to a metal connecting tube 259 (see FIG. 9) communicating with rinse chamber 97. Similarly, drain line 241 also comprises three sections 261, 263 and 265, the middle section 263 being of resilient material and extending around pump head 253. The three sections of drain line 241 are coupled via a retaining bar 267 in the same manner described above in regard to supply line 239. On actuation of pump P1, the pump head 253 rotates in a clockwise direction to stretch sections 252 and 263 of the supply and drain lines, thereby achieving a peristaltic pumping action for circulating cleaning solution through the rinse chamber to clean the outside surface of the needle as it moves from its extended back to its retracted position. For reasons which appear below, the pump remains in operation for a brief interval of time after the needle reaches its fully retracted position in which the tip of the needle is between supply and drain lines 255 and 265.

Means generally designated 269 is operable in conjunction with cleaning means 237 for automatically flushing and cleaning needle passage 69, first and second conduit means 61 and 65, and discharge conduit means 215 after completion of an aspiration cycle, which, as mentioned above, comprises movement of the carriage and needle from their retracted to their extended positions, aspiration of a specimen sample from a container at sampling station 27, and movement of the carriage and needle back to their retracted positions. More specifically, means 269 comprises a second parastaltic pump P2 (FIG. 19) secured to mounting plate 243. This pump comprises a pump head 271 rotatable in a clockwise direction to repetitively stretch and release a resilient section 273 of line 233 extending around the pump head and having its end secured in a retaining bar 275 identical to retaining bars 251 and 267 described above. Thus the requisite peristaltic pumping action is produced to draw cleaning solution from rinse chamber 97 into needle passage 69 and thence through first and second conduit means 61, 65 and discharge conduit means 215 to a suitable waste receptacle. This flushes and cleans the entire system preparatory to the initiation of the next aspiration cycle.

It will be noted that when in its retracted position within rinse chamber 97, the tip of needle 67 is positioned between supply line 255 and drain line 265. Since the diameter of needle 67 is only slightly smaller than the diameter of bore 97 at this point, cleaning solution is drawn into the needle (by the perastaltic pumping action of P2) in short slugs, with air interspersed between the slugs. This intermittent flow of solution through the system is advantageous in that the various conduits are scrubbed to thoroughly clean them.

As mentioned above, a typical aspiration period may be about 6 seconds or even longer if blood viscosity is high (due to low temperatures or high protein content). Under certain circumstances, as when a relatively high-speed analyzer is being used, it may be desirable to reduce the aspiration period. This may be accomplished by increasing the pressure in container C, preferably before aspiration of the specimen sample therefrom, so that during aspiration the specimen sample is "pushed" toward the intake line 5 by the relatively high pressure in container C and "pulled" toward the intake line 5 by the relatively low pressure in conduit means 61 and 65.

Figure 21:
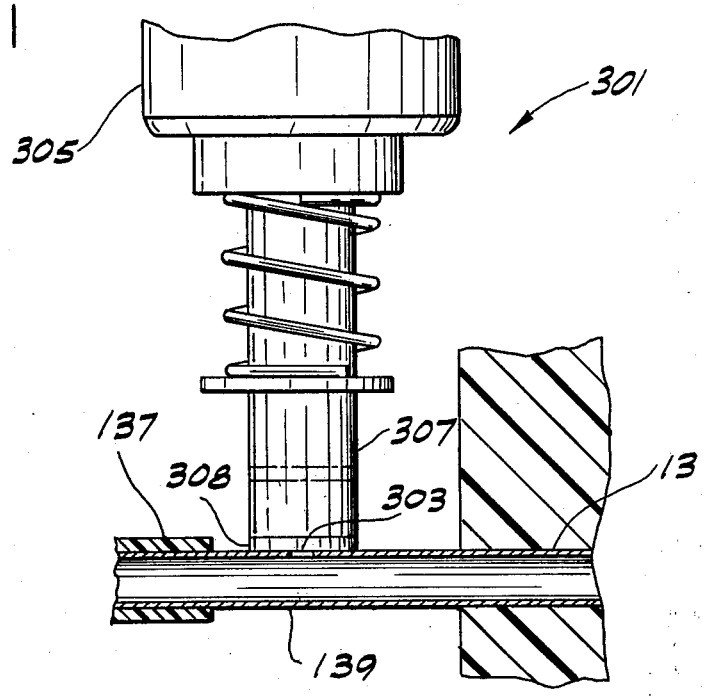
FIG. 21 is a view illustrating optional means of this invention for effecting an increase of the pressure in the container at the sampling station to atmospheric pressure.

Referring now to FIG. 21, means generally indicated at 301 for effecting an increase of the pressure in the container C at the sampling station 27 is shown as comprising an opening 303 at a suitable location in connector tube 139 and valve means constituted by a solenoid valve 305 mounted, for example, on main valve block 129 or on the rear wall 17 of cabinet 13 and having a plunger 307 spring-biased toward an extended position in which it seals the opening 303. Plunger 307 has a seal 308 of suitable resilient material at its lower end. On energization of valve 305, plunger 307 is adapted to move to its retracted position (shown in phantom) in which the interior of tube 139 is exposed to ambient pressure. Solenoid valve 305 is adapted to be energized to move the plunger from its normally extended position to its retracted position when the carriage 79 moves needle 67 to its penetrating position within container C, thereby exposing the interior of the container to the atmosphere via passage means comprising needle inlet 71, needle passage 69, needle outlet 73, line 137, tube 139 and opening 303. Valve 305 is deenergized for movement of plunger 307 back to its extended sealing position prior to the energization of solenoid valve 173 so that when the latter is energized to raise plunger 175 to open line 161, the pressure in conduit means 61 and 65 is reduced for aspirating a sample from container C. The fact that the contents of container C are at atmospheric pressure rather than under a partial vacuum enables the blood specimen to be aspirated more quickly from the container.

It will be understood that the exposure of the contents of container C to atmospheric pressure prior to aspiration may be accomplished in ways other than that described above.

Figure 22:
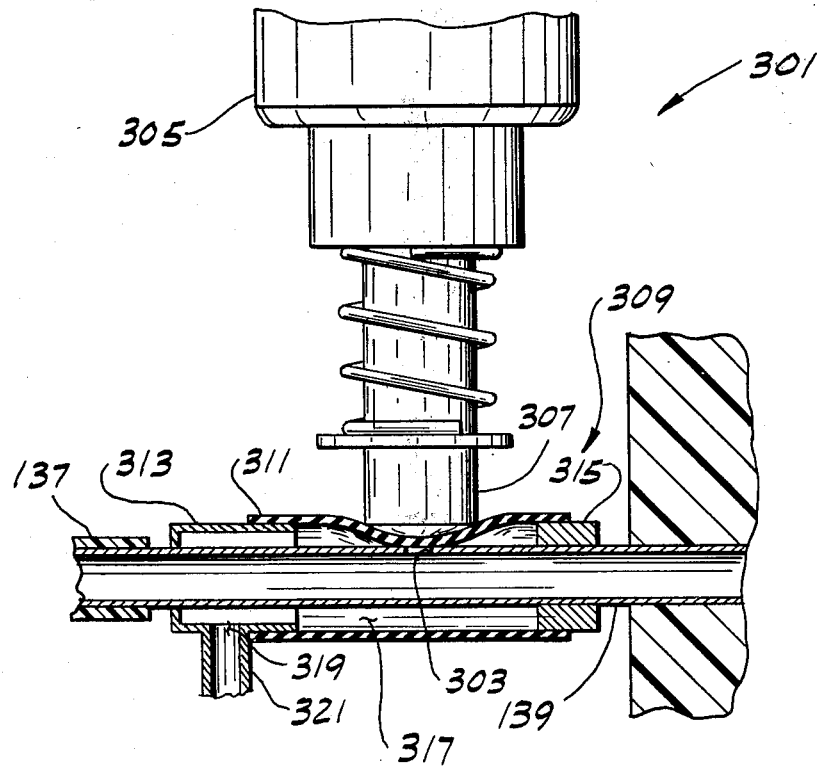
FIG. 22 is a view similar to FIG. 21 showing optional means for increasing the pressure in the container at the sampling station to a pressure greater than atmospheric pressure.

FIG. 22 shows an arrangement for effecting an increase of the pressure in the container at the sampling station 27 to a pressure greater than atmospheric pressure. Thus means designated generally at 309 is provided for enclosing tube 139 at opening 303. More specifically, means 309 comprises a sleeve 311 around tube 139 and plugs 313 and 315 in opposite ends of the sleeve for sealing the annular space 317 around tube 139 between the tube and the sleeve. The latter is of suitable resilient material such as silicone rubber and has an inlet 319 in communication via a line 321 with a source (not shown) of pressurized gas such as air, the annular space around tube 139 thus being, in effect, a pressure chamber.

When in its normally extended position, the plunger 107 of solenoid valve 305 presses the resilient sleeve 311 against opening 303 to close it, thereby preventing the pressurized gas in chamber 317 from entering tube 139. However, when needle 67 moves to its extended position within container C at the sampling station 27, solenoid valve 305 is energized to move plunger 307 to its retracted position, with the resilient sleeve 311 springing away from opening 303. This permits pressurized gas to flow into tube 139 and thence into the container C to pressurize it. Valve 305 is then deenergized whereupon plunger 307 moves back to its normally extended position to seal opening 303 in tube 139. This occurs prior to the energization of solenoid valve 173 so that when the latter is energized to raise plunger 175 to open line 161 the pressure in conduit means 61 and 65 is reduced to aspirate a specimen sample from container C.

It will be understood that container C may be pressurized in ways other than the one described above. For example, a needle separate from needle 67 could be used for introducing pressurized gas into container C. This needle could be operable for penetrating container C to pressurize the container either prior to the container reaching sampling station 27 or after the container has reached the sampling station.

Figure 24A:
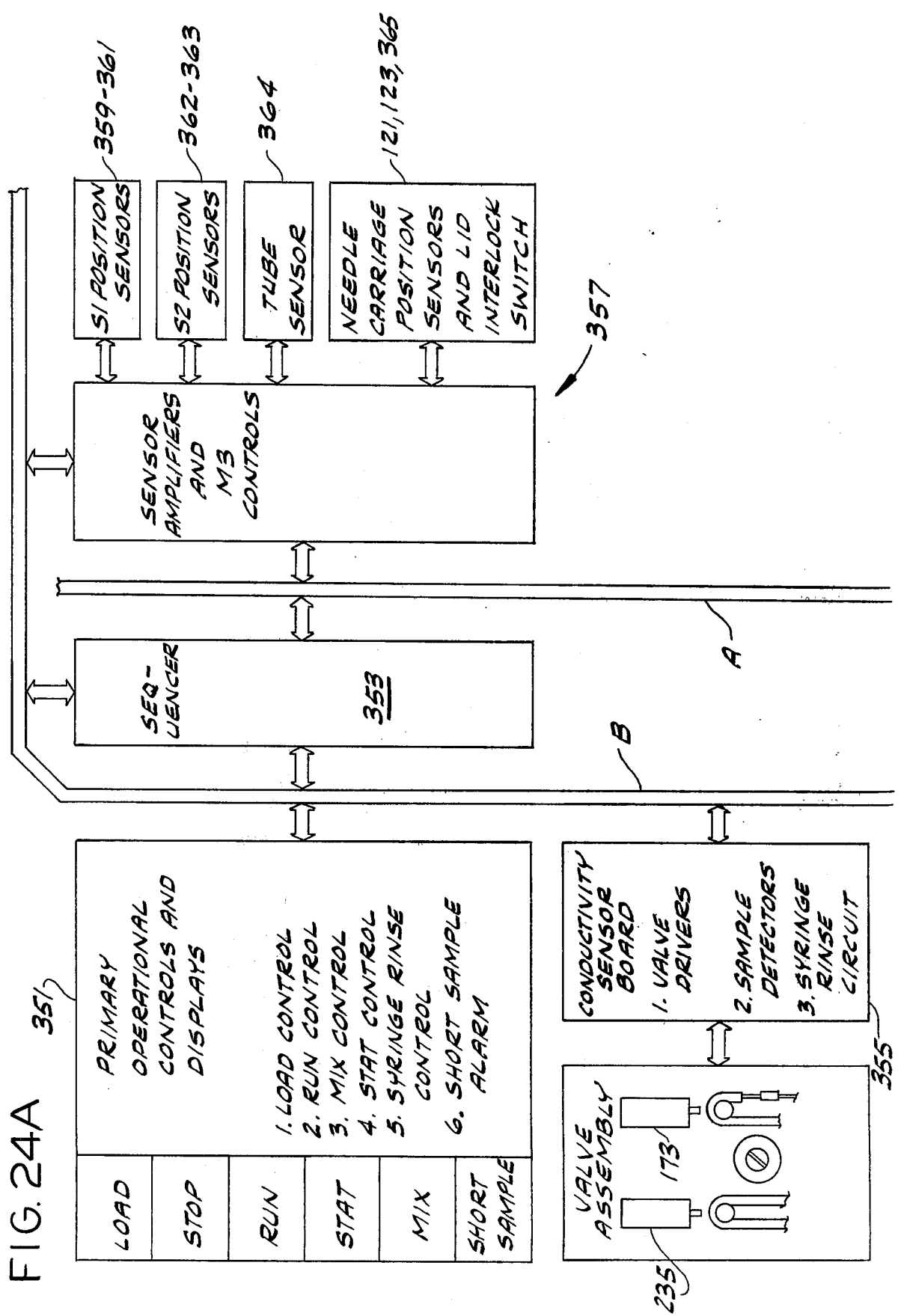
FIGS. 24A and 24B are block diagrams of the electrical circuitry of the apparatus of this invention.
Figure 24B:
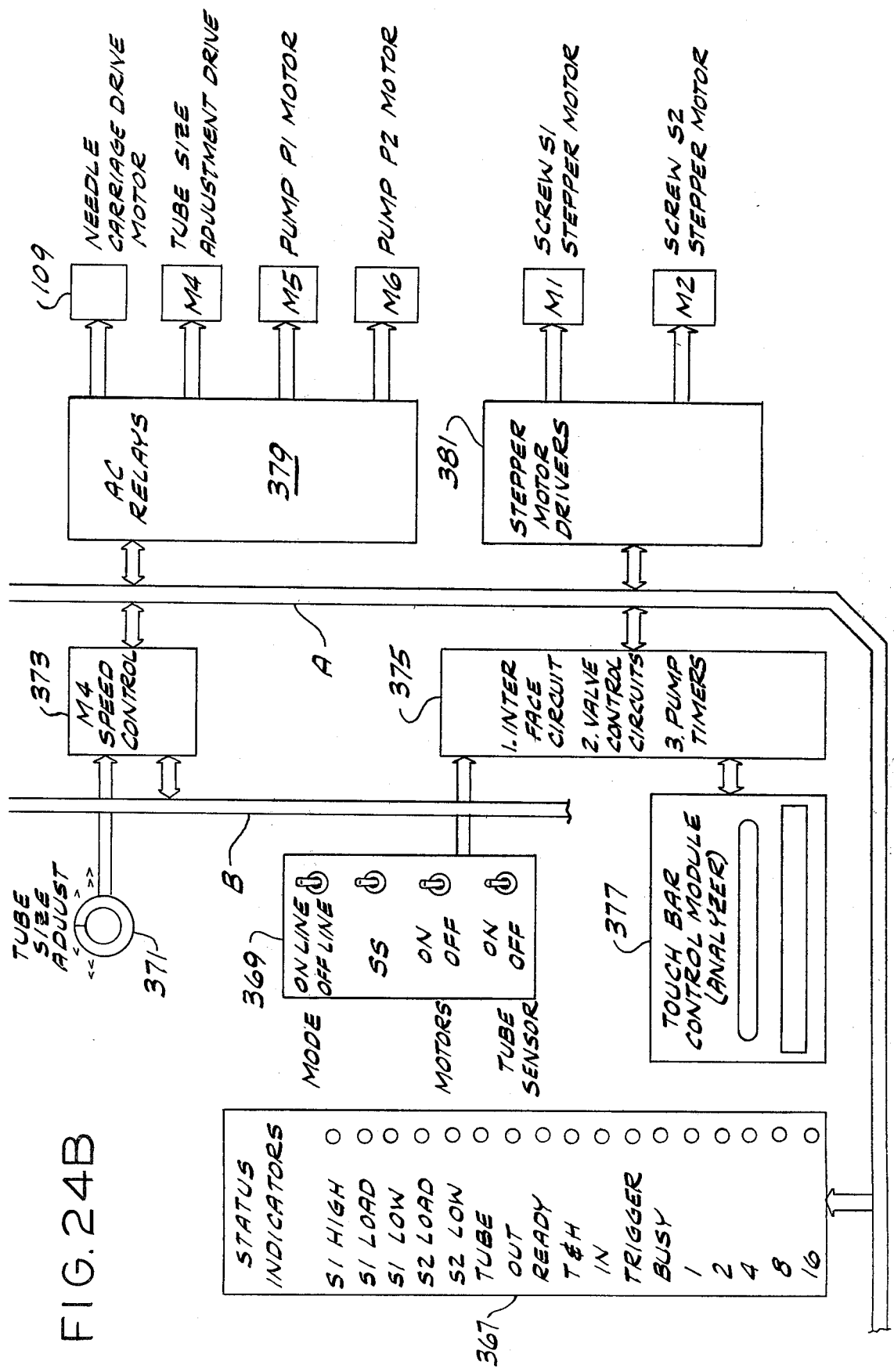

Turning now to FIGS. 24A and 24B, there is shown a block diagram of the electric circuitry for controlling apparatus 1. This circuitry includes a primary operational control section 351 with accompanying displays, a sequencer section 353, solenoid valves 173 and 235, a conductivity sensor section 355, a sensor and needle carriage motor control section 357 (including sensors 359 through 363 for sensing the position of shafts S1 and S2, a sensor 364 for sensing the presence of a tube at the sampling station, needle carriage position sensors 121 and 123 and a lid interlock switch 365), a status indicator section 367 (FIG. 24B), a secondary control section 369, a tube size adjustment section 371, a tube size adjustment motor speed control section 373, an interface section 375, a control module 377 for controlling the analyzer (e.g., the Coulter counter), an A.C. relay section 379, a stepper motor driver section 381, two stepper motors M1 and M2 for driving shafts S1 and S2, needle carriage drive motor 109, a tube size adjustment drive motor M4, and two motors M5 and M6 for pumps P1 and P2 respectively. These sections are disposed on circuit boards and the words boards and sections are used interchangeably herein. Of course, the various sections need not be disposed on distinct circuit boards or in the particular arrangement shown. The sections or boards listed above are electrically connected together by means of two buses, bus A and bus B.

The primary operational control board (see FIGS. 25A and 25B) includes six lighted pushbutton switches labelled Load, Run, Stop, Stat, Mix and Short Sample, which are also shown in FIGS. 1 and 2 on the front of apparatus 1. The first five of these switches (i.e. all but the Short Sample switch) are connected through a diode matrix 383 to the inputs of four bistable circuits or flip-flops FF1–FF4 whose outputs are decoded by a decoding circuit indicated generally at 385. The outputs of decoding circuit 385 are supplied to the bases of a set of six NPN transistors Q1 whose emitter-collector circuits are connected between ground and a set of six indicator lights labelled LOAD, RUN, STOP, STAT, MIX and SHORT SAMPLE, these indicator lights being the lights in the aforementioned pushbutton switches having the corresponding labels. As is explained below, actuation of a particular pushbutton switch causes the corresponding indicator lamp to light, among other things. Also shown on FIG. 25B is a first 555 timer 387 for supplying a 10 Hz square wave to the LOAD lamp, a second 555 timer 389 for supplying a 570 Hz square wave to all six indicator lamps, a siren 391, and alarm circuitry 393 for sounding said alarm under specified conditions, discussed below. Timer 389 is used because the six indicator lamps are rated for 6 V operation but are operated off a 9 V supply.

Control board 351 also includes a capacitor 395 connected to the diode matrix and, through a resistor and a line L1 to a +5 V regulator 397. When power is supplied to the apparatus, this capacitor begins charging, thereby momentarily supplying a logic Low signal to the reset inputs of flip-flops FF3 and FF4 (the STAT and Mix flip-flops) and to the set inputs of flip-flops FF1 and FF2 (the Load and Run flip-flops). This start-up signal is also supplied via a connector C1 to the rest of the circuitry. (Although a single connector C1 is shown, it should be appreciated that the actual start-up signal may be supplied to one or more lines of each bus.) Referring specifically to flip-flops FF1–FF4, upon start-up the Q output of flip-flop FF1 goes to a logic Low, the Q output of flip-flop FF2 becomes a logic High, and the Q outputs of flip-flops FF3 and FF4 are both Low. These outputs are supplied to decoding circuit 385.

The $\overline{Q}$ output of flip-flop FF1 is supplied via a line L3 to an inverter 399 whose output is supplied to a pair of NAND gates G1 and G3 and to a connector C3. The other inputs to gates G1 and G3 are supplied, either directly or in inverted form, from a connector C5. This particular connector, as is explained below, is at a logic Low when shafts S1 and S2 are in the load position (and the signal indicating that fact is not inhibited) and is otherwise at a High logic level. If shafts S1 and S2 are in the load position (i.e., in such relative position that a tube inserted therebetween is horizontal), which will be the case unless a malfunction has occurred, both inputs to gate G3 will be High and its output will be Low. This output is supplied to a NAND gate G5, causing its output to go High. The output of gate G5 is supplied to a NAND gate G7, the other input of which is the 570 Hz output of timer 389. The resulting pulsed output of gate G7 is inverted and supplied to the base of Load lamp transistor Q1, causing the Load lamp to be (apparently) continuously lit. If shafts S1 and S2 are not both in the load position, connector C5 is High, which causes the output of gate G3 to be High and which causes the output of gate G1 to be Low. The output of gate G1 is inverted and supplied to a NAND gate G9, the other input of which is the 10 Hz output of timer 387. The output of gate G9 is, accordingly, a 10 Hz pulse train. This output is supplied via gates G5, G7 and an inverter to the base of Load lamp transistor Q1, causing the Load lamp to flash, indicating to the operator that the shafts are not in proper position for loading specimen tubes.

Likewise, the Q output of flip-flop FF2, the Run flip-flop, is supplied via a line L5 to a line L7, to an inverter 401, and to a NAND gate G11. The other input to gate G11 is the 570 Hz output of timer 389, so when the Q output of flip-flop FF2 is High, the output of gate G11 is a train of 570 Hz pulses. These pulses are inverted and supplied to the base of Run lamp transistor Q1, causing the Run lamp to light. The output of inverter 401 is Low in this case. This Low is supplied to a connector C7 and to a NAND gate G13. The other input of gate G13 is connected to a connector C9, but irrespective of that the Low from inverter 401 causes the output of gate G13 to be High. This High is inverted and the resulting Low is supplied to a NAND gate G15, causing its output to be High. The output of gate G15 is inverted and the resulting Low is supplied to the base of the Stop lamp transistor Q1. Since this transistor does not conduct, the Stop lamp does not light.

The Q output of flip-flop FF3 (the Stat flip-flop), which is Low during start-up, is supplied via a line L9 to a line L11 and to an inverter 403. Line L11 in turn is directly connected to an input of a NAND gate G17. Since this line is Low, the output of gate G17 is High. This High is inverted and the resulting Low is supplied to the base of Stat lamp transistor Q1, causing the Stat lamp to remain unlit. The output of inverter 403 is supplied to a connector C11. Likewise, the Q output of the Mix flip-flop, flip-flop FF4, is supplied via a line L13 to a line L15 and to an inverter 405. The Low on these lines is supplied to a NAND gate G19, causing its output to go High and thereby causing the corresponding Mix lamp to remain unlit. The output of inverter 405 is supplied to a connector C13.

When a short sample is detected, see discussion below, a signal (logic High) indicating that fact is supplied via a connector C15 to an input of a NAND gate G21, causing the Short Sample lamp to appear to be continuously lit.

The alarm circuitry includes a 555 timer 407 configured to provide a 10–15 Hz output, and a second 555 timer 409 configured to provide a 320 Hz output to the base of a transistor Q3 which has its collector-emitter circuit connected to siren 391. The inputs to circuit 393 include a connector C17 which is called the Runline (the Runline is normally High during operation of the apparatus and when it is brought Low causes various functions of the apparatus to halt), the output of inverter 401, a connector C19 which carries a signal which blocks the alarm during rinse of the syringe (generated by circuitry not shown), and the output of the Run flip-flop which is supplied to circuit 393 by line L7. If desired, connector C19 can be connected to an additional logic gate instead of the diode shown. Briefly, the siren sounds if the Runline goes Low (except in the case of syringe rinse), which can occur in the case of a short sample or in the case of a sluggish sample, as is discussed below.

Figure 25A:
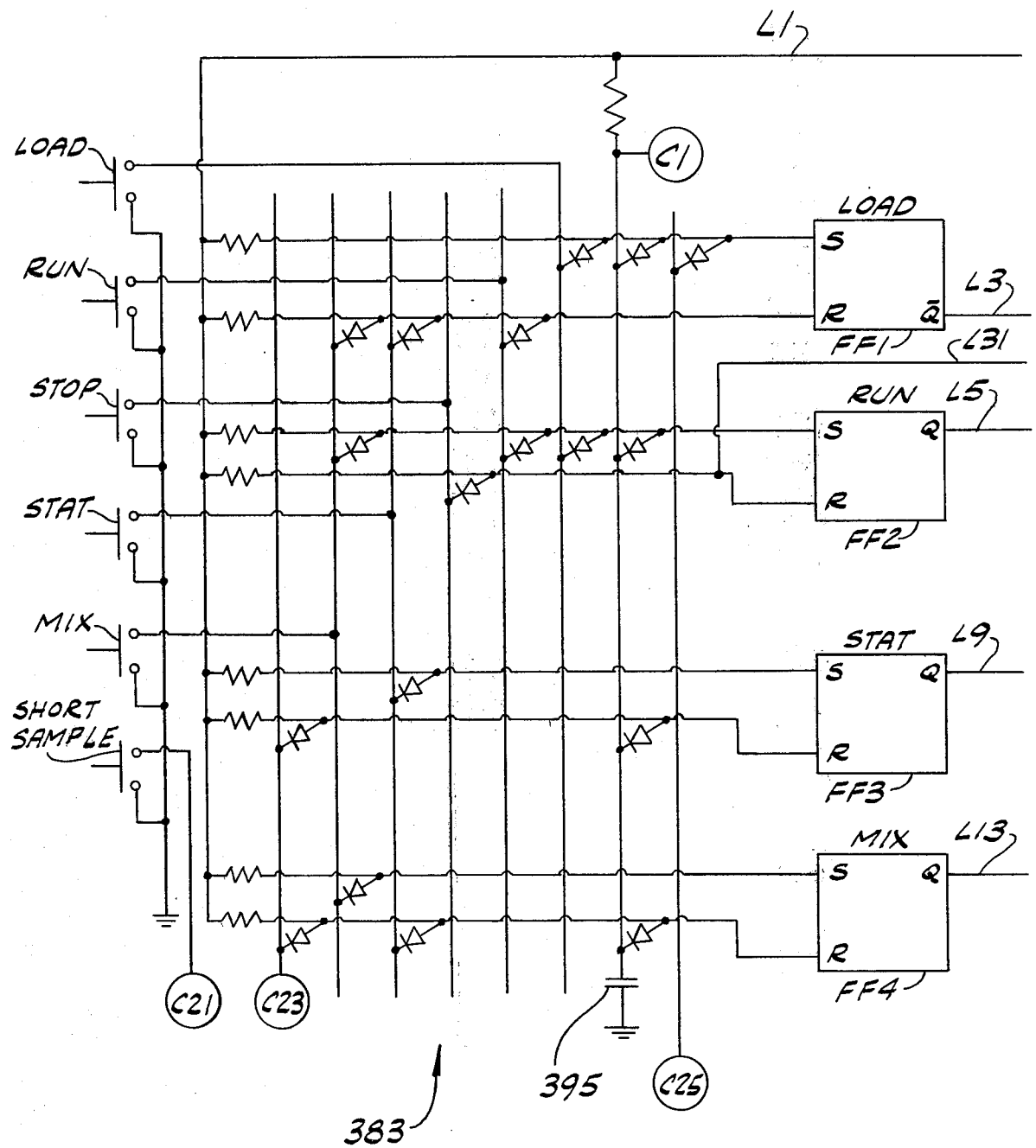
FIGS. 25A and 25B are schematic diagrams of a portion of the electrical circuitry of the apparatus of this invention, including a number of user operable switches and associated circuitry.
Figure 25B:
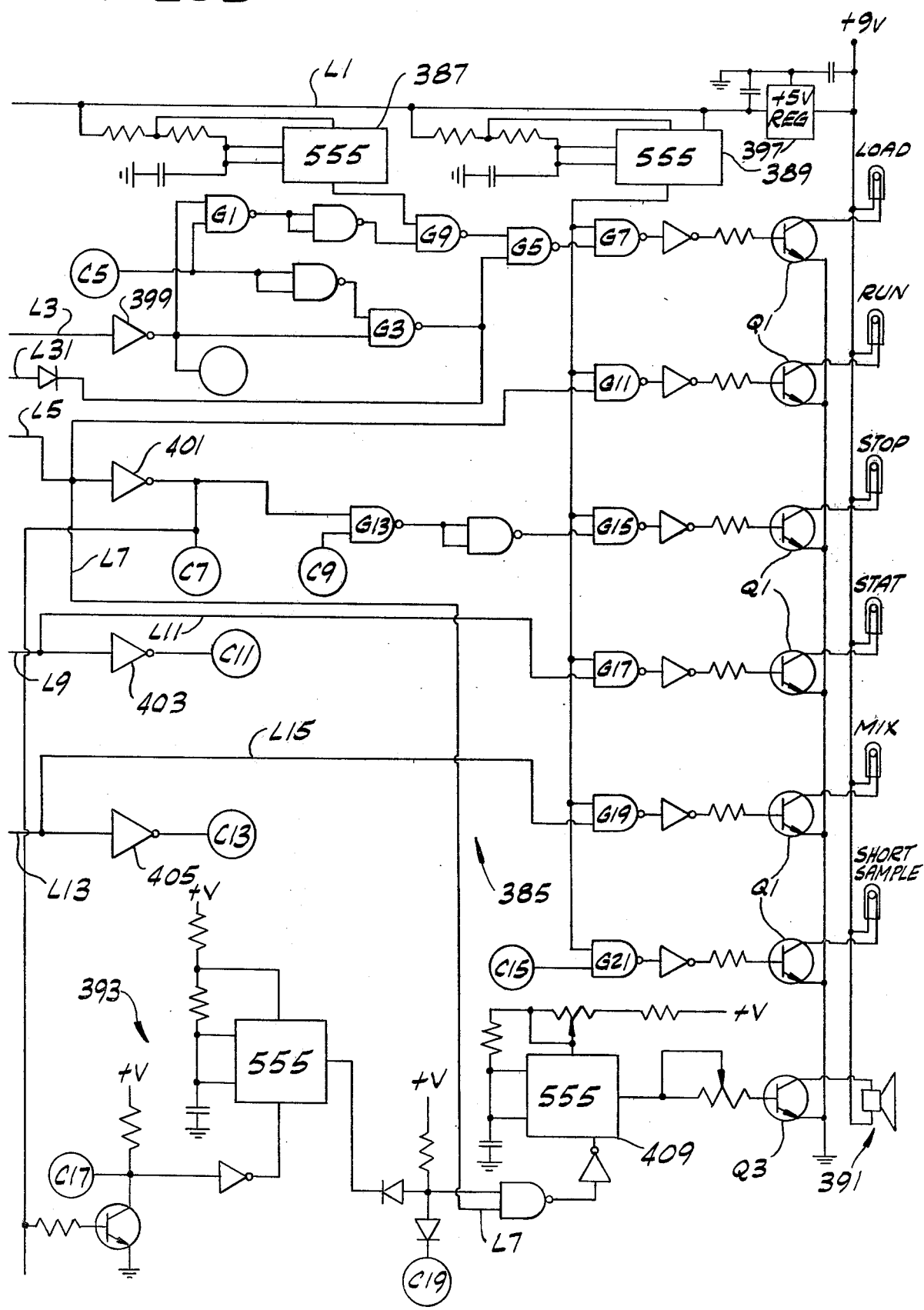
Figure 26A:
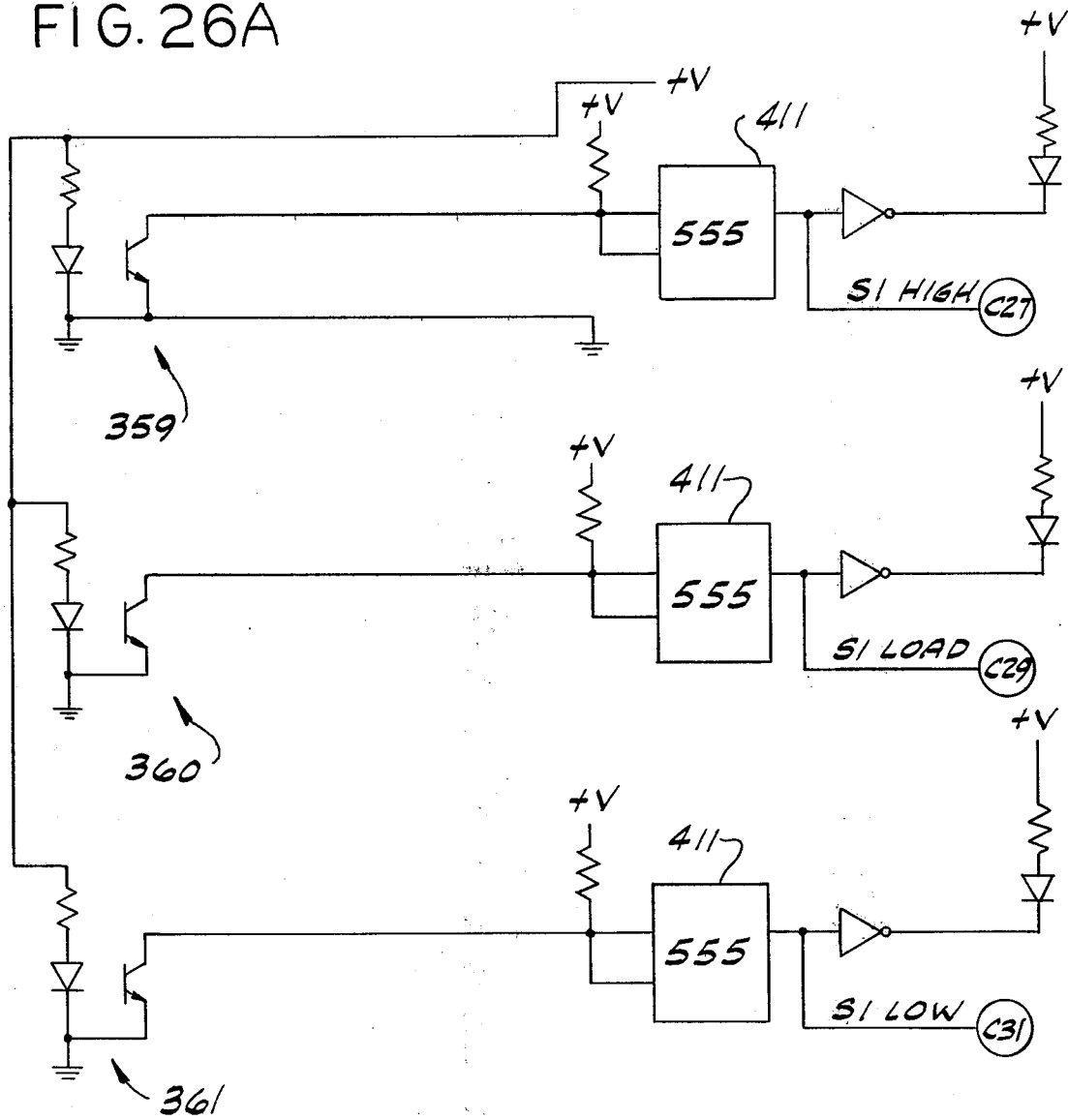
FIGS. 26A–26E are schematic diagrams of various sensor circuits and a motor control circuit used in the apparatus of this invention.
Figure 26E:
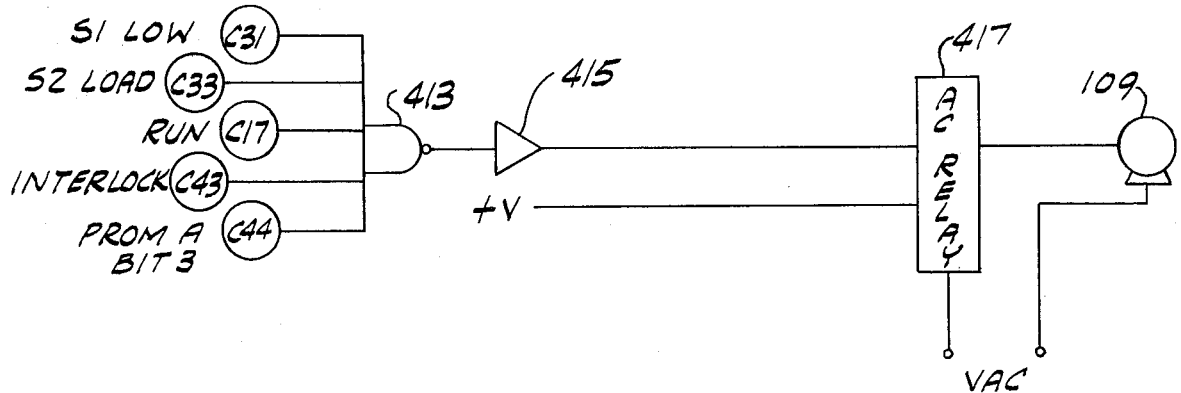
Figure 26B:
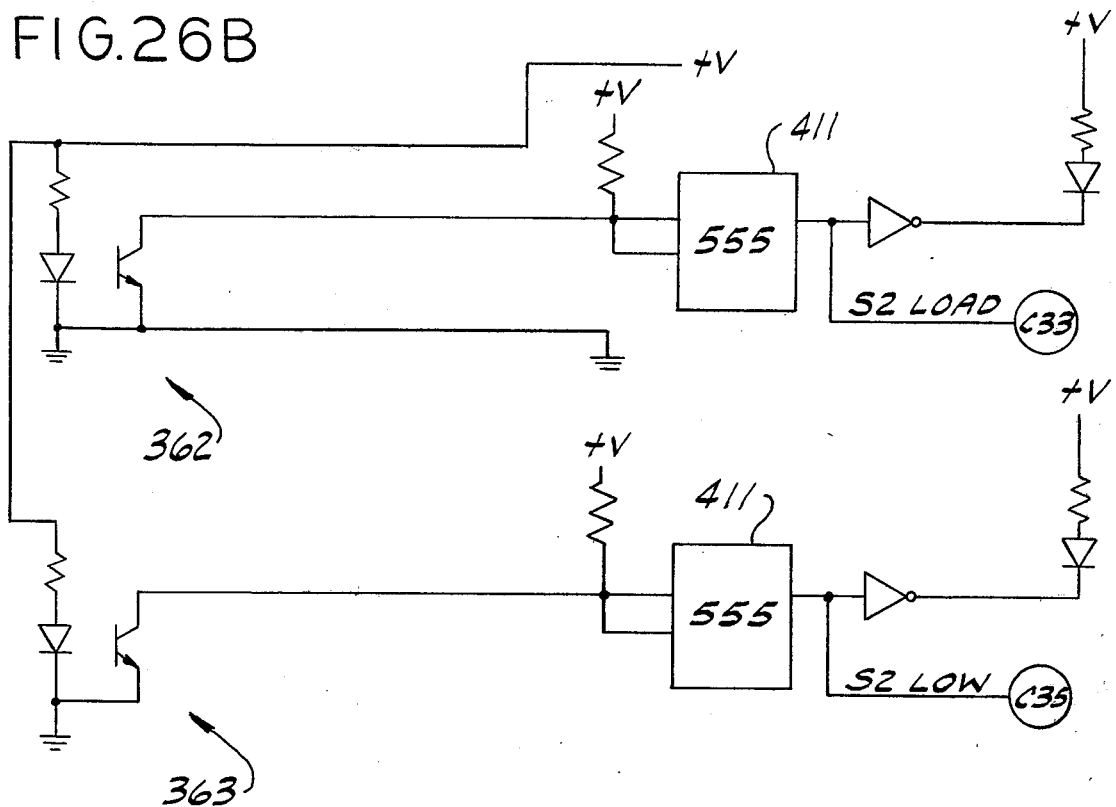
Figure 26C:
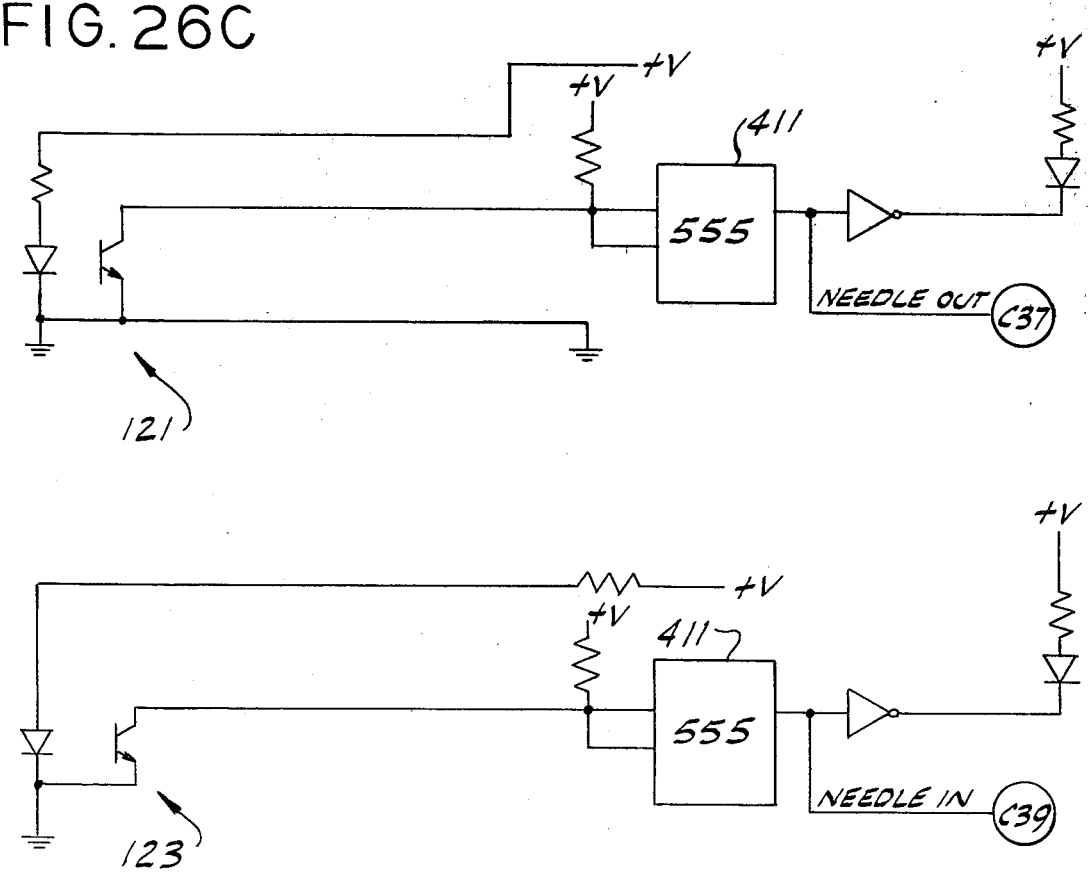

Also shown on FIG. 25A are connectors C21 (connected to the short sample switch), C23 (for providing reset signals to the Mix and Stat flip-flops), and C25 (for supplying an automatic stop signal to the Load flip-flop). The short sample switch, when actuated, connects connector C21 directly to ground. Actuation of the Mix switch sets the Mix flip-flop, sets the Run flip-flop, and resets the Load flip-flop, by bringing the respective inputs of said flip-flops Low. Likewise, actuation of the Stat switch resets the Mix flip-flop, sets the Stat flip-flop, sets the Run flip-flop, and resets the Load flip-flop. Actuation of the Stop switch resets the Run flip-flop. Actuation of the Run switch resets the Load flip-flop and sets the Run flip-flop. And actuation of the Load switch sets the Load and Run flip-flops.

The sensors and needle carriage motor control section are shown in FIGS. 26A–26E. The sensors are opto-electronic sensors consisting of a light-emitting diode (LED) in combination with a phototransistor. The opto-electronic sensors sold under the trade designation TIL 138 by Texas Instruments, Inc. of Dallas, Texas are suitable. Each sensor is connected between a source of voltage and ground so that the LED emits light (infrared light in the case of the TTL 138). The collector of each phototransistor is connected to pins 2 and 6 of a corresponding 555 timer 411, configured as a Schmitt trigger. The output of each Schmidt trigger 411 is a function of whether its associated sensor senses an object between its LED and phototransistor. When an object is present, the output of the corresponding trigger is a logic High (e.g., 5 volts), but when no object is present the output is Low (e.g., 0 volts). Sensors 359, 360 and 361 (see FIG. 26A) detect whether shaft S1 is at its high, load, or low positions, respectively. Signals representing these facts are supplied from the corresponding triggers, via connectors C27, C29 and C31 to the rest of the circuitry. Sensors 362 and 363 (see FIG. 26B) detect when shaft S2 is at its load or low positions respectively and signals representing these conditions are supplied from the corresponding triggers 411 to the rest of the circuitry via connectors C33 and C35. Sensors 121 and 123 (see FIG. 26C) detect when the needle carriage is in its "out" and "in" positions respectively and signals representing these conditions are supplied from triggers 411 to the rest of the circuitry via connectors C37 and C39. Likewise, tube sensor 364 (see FIG. 26D) senses the presence of a tube at the sampling station and a signal representing the presence or absence of a tube at the station is supplied from trigger 411 via a connector C41 to the rest of the circuitry.

The control for the needle carriage drive motor (see FIG. 26E) includes an eight-input NAND gate 413 (only five of which inputs are used), a buffer 415 and a Motorola MP120D3 type A.C. relay 417. Motor 109 is inhibited unless all the inputs to gate 413 are High. These inputs include signals indicating that shaft S1 is in the Low position (on connector C31), that shaft S2 is in the Load position (on connector C33), that the apparatus is in the Run mode (on the Runline, connector C17), and that the door of the apparatus is closed (on a connector C43). Gate 413 also receives a signal from the sequencer board (via a connector C44), described below, which signal is High only when the sequence of operations of the apparatus requires the needle carriage drive motor to be energized.

Figure 27A:
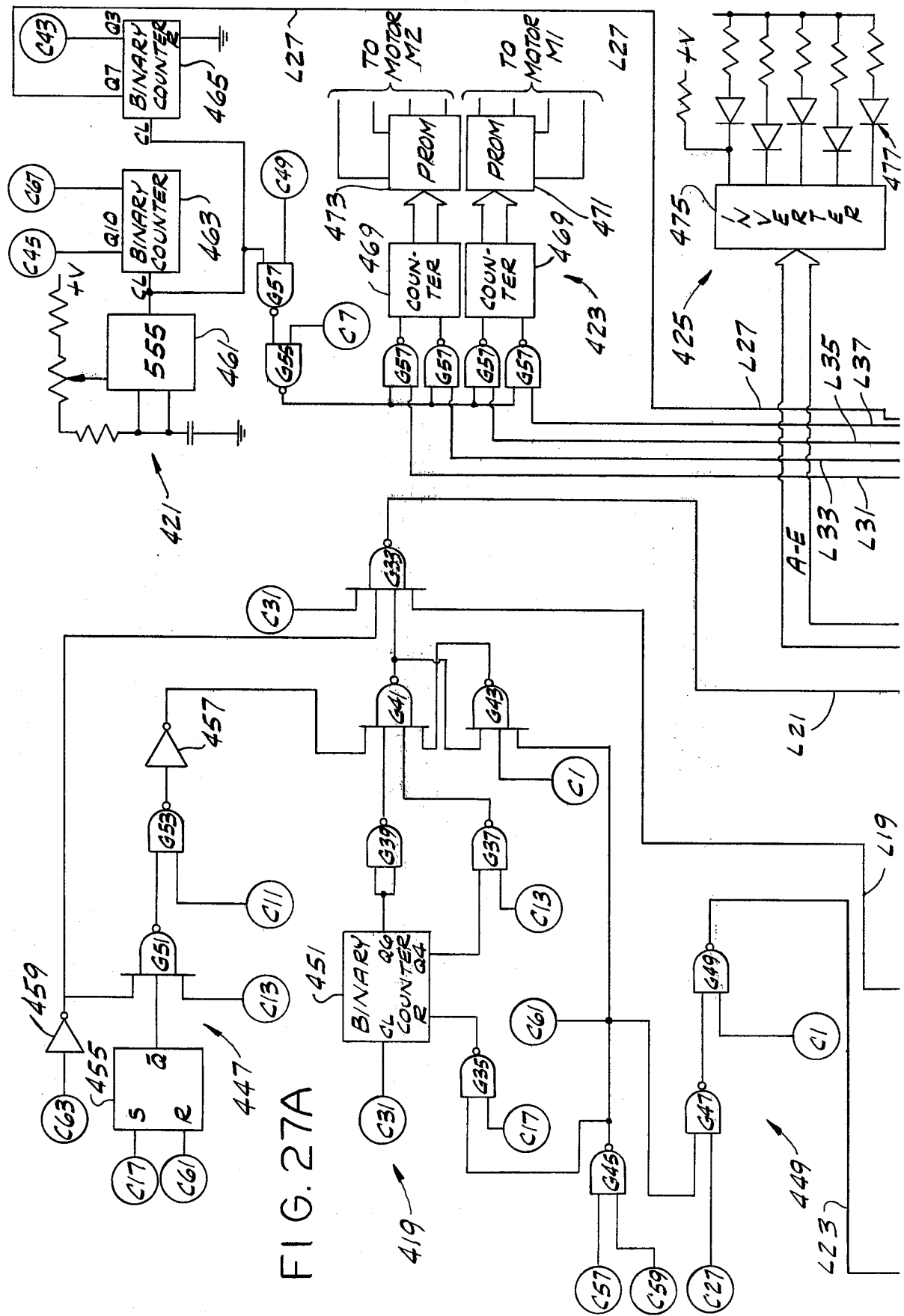
FIGS. 27A and 27B are schematic diagrams of the sequence control circuitry used in the apparatus of the present invention.
Figure 27B:
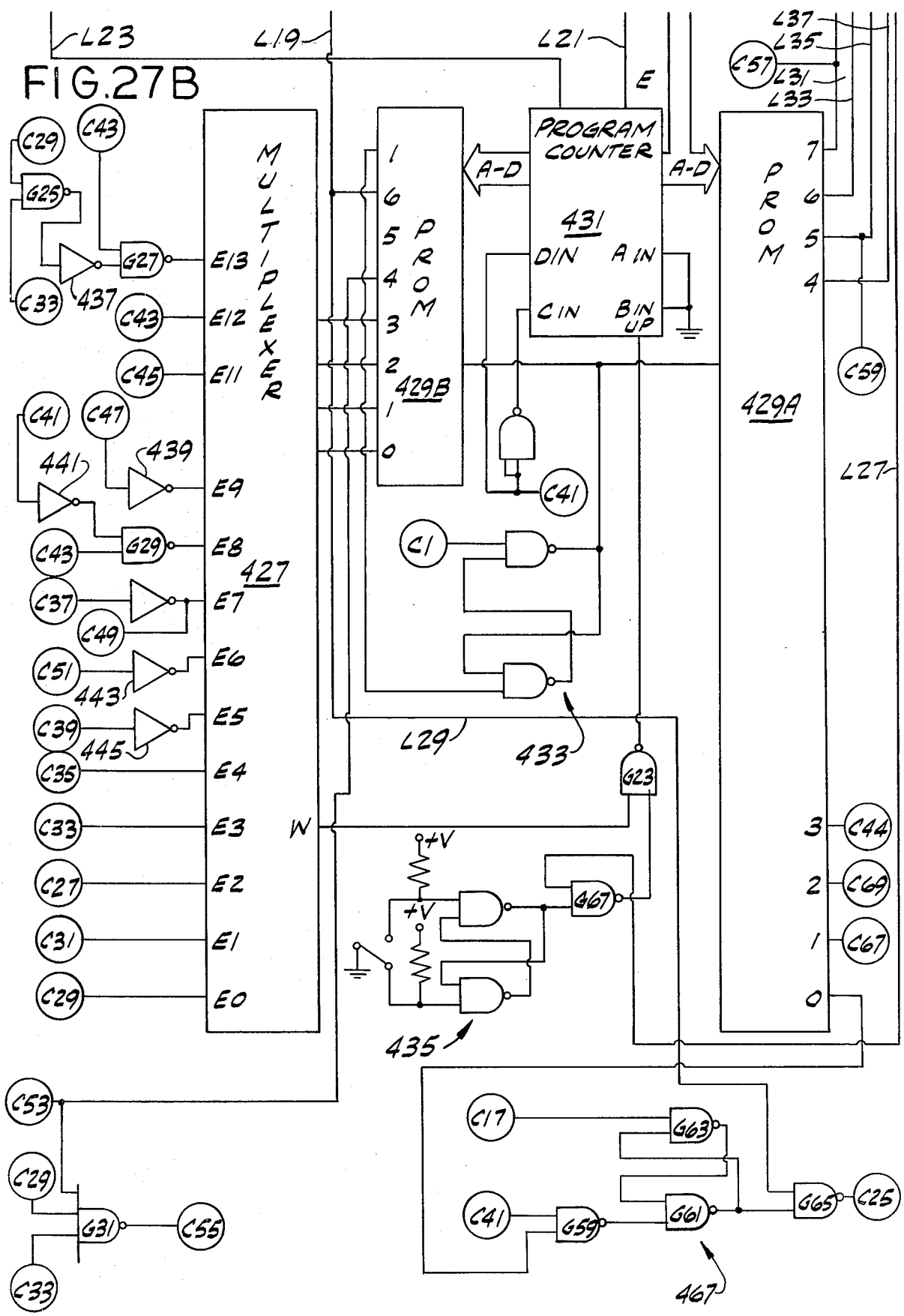

The sequencer itself (see FIGS. 27A and 27B) includes a tilt-and-hold request circuit 419, a clock circuit 421, a stepper motor control section 423, a program status display circuit 425, a multiplexer 427, two programmable read only memories (PROMs) 429A and 429B, a program counter 431, a start-up flip-flop 433, and a single-step control circuit 435.

The sequencer has a program which is stored in PROMs 429A and 429B. These PROMs, like others described below, are tri-state output devices and require 2 K pull-up resistors (connected to +5 v) to pull high each output. The contents of these PROMs are as follows:

| Bits | PROM A | | | | | | | |
|---|---|---|---|---|---|---|---|---|
| | 7 | 6 | 5 | 4 | 3 | 2 | 1 | 0 |
| Step (Hexadecimal) | | | | | | | | |
| 00 | 0 | 0 | 1 | 0 | 0 | 1 | 1 | 0 |
| 01 | 0 | 0 | 1 | 0 | 0 | 1 | 1 | 0 |
| 02 | 0 | 0 | 0 | 1 | 0 | 1 | 1 | 0 |
| 03 | 0 | 0 | 0 | 1 | 0 | 1 | 1 | 0 |
| 04 | 0 | 0 | 0 | 0 | 0 | 1 | 1 | 0 |
| 05 | 0 | 0 | 0 | 0 | 1 | 0 | 1 | 0 |
| 06 | 0 | 0 | 0 | 0 | 0 | 0 | 0 | 0 |
| 07 | 0 | 0 | 0 | 0 | 1 | 1 | 1 | 0 |
| 08 | 0 | 0 | 0 | 0 | 0 | 1 | 1 | 1 |
| 09 | 1 | 0 | 0 | 0 | 0 | 1 | 1 | 0 |
| 0A | 1 | 0 | 1 | 0 | 0 | 1 | 1 | 0 |
| 0B | 1 | 0 | 1 | 0 | 0 | 1 | 1 | 0 |
| 0C | 1 | 0 | 1 | 0 | 0 | 1 | 1 | 0 |
| 0D | 0 | 1 | 0 | 0 | 0 | 1 | 1 | 0 |
| 0E | 0 | 0 | 0 | 1 | 0 | 1 | 1 | 0 |
| 0F | 0 | 0 | 0 | 1 | 0 | 1 | 1 | 0 |

-continued

| Bits | PROM A | | | | | | | |
|---|---|---|---|---|---|---|---|---|
| | 7 | 6 | 5 | 4 | 3 | 2 | 1 | 0 |
| 10 | 0 | 0 | 0 | 0 | 0 | 1 | 1 | 0 |
| 11 | 0 | 0 | 0 | 0 | 0 | 1 | 1 | 0 |

| Bits | PROM B | | | | | | | |
|---|---|---|---|---|---|---|---|---|
| | 7 | 6 | 5 | 4 | 3 | 2 | 1 | 0 |
| Step (Hexadecimal) | | | | | | | | |
| 00 | 1 | 0 | 1 | 1 | 0 | 0 | 0 | 0 |
| 01 | 1 | 1 | 1 | 1 | 0 | 0 | 0 | 1 |
| 02 | 1 | 0 | 1 | 1 | 0 | 0 | 0 | 0 |
| 03 | 1 | 0 | 1 | 1 | 1 | 1 | 1 | 1 |
| 04 | 1 | 0 | 0 | 1 | 1 | 0 | 0 | 0 |
| 05 | 1 | 0 | 0 | 0 | 0 | 1 | 0 | 1 |
| 06 | 1 | 0 | 0 | 0 | 1 | 0 | 1 | 1 |
| 07 | 1 | 0 | 0 | 0 | 0 | 1 | 1 | 1 |
| 08 | 1 | 0 | 0 | 0 | 1 | 1 | 0 | 0 |
| 09 | 1 | 0 | 0 | 0 | 0 | 1 | 0 | 0 |
| 0A | 1 | 0 | 0 | 0 | 1 | 1 | 0 | 0 |
| 0B | 1 | 0 | 0 | 0 | 0 | 0 | 0 | 0 |
| 0C | 1 | 0 | 0 | 0 | 0 | 0 | 0 | 1 |
| 0D | 1 | 0 | 0 | 1 | 0 | 0 | 1 | 1 |
| 0E | 1 | 0 | 0 | 1 | 0 | 0 | 0 | 0 |
| 0F | 1 | 0 | 0 | 1 | 0 | 0 | 1 | 0 |
| 10 | 1 | 0 | 0 | 1 | 1 | 1 | 0 | 1 |
| 11 | 0 | 0 | 0 | 1 | 1 | 1 | 1 | 1 |

These PROMs are 32 words × 8 bit memories, such as Texas Instrument's type 54S288 memories. All the bits of PROM 429A and bits 4, 6 and 7 of PROM 429B are used for control of the apparatus. Bits 0-3 of PROM 429B are supplied to the address inputs of multiplexer 427 (a sixteen-line to one-line Signetics type 74150 multiplexer), thereby selecting at any one time only one of the inputs of the multiplexer. Only thirteen of the input pins have inputs shown and only eleven are actually used in the present embodiment. The output of the multiplexer (pin W) is supplied via a NAND gate G23 to the count "up" input of program counter 431, a Signetics 74193 type 4-bit binary counter with present inputs. In this way the program remains at a desired step until the apparatus, as reflected by the inputs to the multiplexer, is in a desired state.

The various inputs to the multiplexer are as follows: The thirteenth input, labelled E13, is supplied from a logic circuit which includes an inverter 437 and a pair of NAND gates G25 and G27. The inputs to gate G25 are connected, via connectors C29 and C33 to the sensor circuits for sensing the load positions of shafts S1 and S2. When both shafts are in the load position, both inputs are High and the output of gate G25 is Low. This output is inverted by inverter 437 and the resulting High is supplied to one input of gate G27. The other input of gate G27 is supplied, via a connector C43, from clock 421. When both inputs are High, the output of gate G27 goes Low. If input E13 is selected by PROM 429B, the inverse of input E13 will thereupon appear at output W. Thus, when the shafts are in the load position, the clock input to gate G27 is High, and input E13 is selected, output W of the multiplexer is High. The signals supplied to inputs E12 and E11 of the multiplexer are also signals from the clock. The first is supplied to input E12 via connector C43. The second represents a delay of approximately six seconds and is supplied via a connector C45 to input E11. Input E9 is shown connected to a connector C47 and an inverter 439, but that input is not used in the present embodiment of the invention.

Input E8 to the multiplexer is connected to a logic circuit comprising an inverter 441 and a NAND gate G29. The inverter is supplied a signal via connector C41 from the tube sensor circuit. When a tube is present at the sampling station, this signal is Low. The inverter output is therefore High. This High output is supplied to gate G29. The other input of gate G29 is a clock input supplied via connector C43. When this is High as well, the output of gate G29, and input E8 of the multiplexer, is Low. The signal supplied to input E7 is the inverted output of carriage "out" position sensor 121 (this signal is supplied to the inverter via connector C37). The inverted signal is also supplied via a connector C49 to the rest of the circuitry. A connector C51 is connected via an inverter 443 to input E6, but this input is not used.

The signal denoting the presence of the carriage at the needle "in" position is supplied via connector C39 and an inverter 445 to input E5 of the multiplexer. And the signals representing shaft S2 in the low position, shaft S2 in the load position, shaft S1 in the high position, shaft S1 in the low position, and shaft S1 in the load position are supplied via connectors C35, C33, C27, C31 and C29 to inputs E4-E0 respectively.

As stated above, bits 0-3 of PROM 429B address the desired inputs of multiplexer 427. Bit 4 of this PROM controls solenoid valve 173 by supplying a signal corresponding to the desired state of said valve to a connector C53. This signal is also supplied to a NAND gate G31, the other two inputs of which are signals (supplied via connectors C29 and C33) indicating whether the shafts are in the load position. If all three inputs of gate G31 are High, its output goes Low, which Low is a signal that the apparatus is in the load condition. This signal is supplied to the rest of the circuitry via a connector C55.

Bit 6 of PROM 429B controls the tilt-and-hold function of the apparatus (Tilt-and-hold is that step in the operation of the apparatus wherein the specimen tube to be sampled is tilted to the position shown in FIG. 2 and held there for insertion of needle 67 therein). More specifically, bit 6 of PROM 429B is supplied via a line L19 to one input of a NAND gate G33 in tilt-and-hold circuit 419. If this bit is Low, the other inputs to gate G33 are inhibited and the output of the gate is High. The output of gate G33 is supplied via a line L21 to the Load input of program counter 431. When this signal is Low, which occurs under conditions discussed below, the counter jumps to a preset address; otherwise it continues counting in the normal fashion. The preset address is either "4" or "8" and is determined by tube sensor 364. The signal from this sensor is supplied via connector C41 directly to the D input of the program counter and, in inverted form, to the C input. When a tube is present, the preset address is 4 and the counter jumps to that step. When a tube is not present, the counter jumps to step 8.

The other inputs to gate G33 are derived from circuit 419 and from a logic circuit 447. Circuit 419 includes a program-counter reset section 449, a 12-stage binary counter 451 which serves as a timer for the mix cycle, five NAND gates G35, G37, G39, G41, and G43, and gate G33. Counter reset section 449 in turn includes three NAND gates G45, G47 and G49. Gate G45 has two inputs, one supplied via a connector C57 from bit 7 of PROM 429A and the other supplied via a connector C59 from bit 5 of the same PROM. Both of these bits must be High for the output of gate G45 to be Low. When this occurs (in step A (hexadecimal) of the program), the Low output of gate G45 causes the output of gate G35 to go High, resetting binary counter 451. Thus, the mix cycle timer is reset in step A (hexadecimal) of the program. The output of gate G45 is also supplied to gates G43 and G47 and to a connector C61. The other input to gate G47 is a signal, supplied via connector C27, from sensor 359 indicating whether shaft S1 is in the High position. The output of gate G47 is supplied to gate G49, the other input of which is connector C1, the start-up signal. Whenever either of these inputs is Low, the output of gate G49 is High. This High, supplied on a line L23 to the reset input of the program counter, resets said counter. Thus, the program counter is reset during start-up and after step F (hexadecimal) of the program (step F being the first step after step A after which shaft S1 reaches its High position).

The other input to gate G35, which resets binary counter 451, the (mix cycle timer), is the runline, connector C17. Thus, when the runline goes Low the mix cycle timer is reset. The clock input to the mix cycle timer is connected via connector C31 to circuit 361. Thus, every time shaft S1 reaches its low position, counter 451 is incremented. After 8 counts, the Q4 output of counter 451 goes High. This output is supplied to gate G37. The other input to gate G37 is supplied via connector C13 from the mix flip-flop (see FIG. 25A). If the Mix switch has been actuated, connector C13 is Low, thus inhibiting gate G37. If not, the output of gate G37 goes Low, causing the output of gate G41 to go High. This High is supplied to one input of gate G33. When all the other inputs of gate G33 are High as well, its output goes Low, causing the program counter to jump (as described above) to either step 4 or step 8 of the program. These other inputs to gate G33 include the signal (on connector C31) indicating that shaft S1 is in the low position, which is the sampling position, an inverted signal via a connector C63 indicating the status of a flip-flop associated with pump P2, and the previously discussed signal on line L19 from bit 6 of PROM 429B. This bit is High only in step 1 of the program, so only in that step can a tilt-and-hold request reach the program counter.

If the Mix flip-flop has been set, C13 is low, the output of gate G37 is High and that of gate G41 is Low. In this case, the program counter does not jump to step 4 or 8 until the Q6 output of mix cycle counter 451 goes High (which occurs after 32 cycles). This High is inverted by gate G39 and the Low output of that gate ultimately causes the program counter to jump as before.

The other two inputs to gate G41 are from circuit 447 and from gate G43. Circuit 447 includes a flip-flop 455, two NAND gates G51 and G53, and two inverters 457 and 459. The set input of the flip-flop is connected to connector C17, the runline, and the reset input is connected to connector C61 which carries a signal indicating that the program is in steps A–C (hexadecimal) which, as discussed below is a feed cycle. The Q output of flip-flop 455 is supplied to one input of gate G51, the other two inputs of which are the output of inverter 459 and connector C13 (the output of the mix flip-flop). The output of gate G51 is in turn supplied to one input of gate G53, the other input of which is connector C11 (the output of the Stat flip-flop). The output of gate G53 is inverted by inverter 457 and thereafter supplied to gate G41.

Gates G41 and G43 are arranged in a flip-flop configuration. The inputs to gate G43 can be considered reset inputs and include the output of gate G45, already discussed, and the start-up signal on connector C1.

Clock 421 includes a 555 timer 461, two twelve-stage binary counters 463 and 465, and a pair of NAND gates G55 and G57. The timer supplies pulses to the clock inputs of both counters. The reset input of counter 463 is connected via a connector C67 to bit 1 of PROM 429A. Since this bit is normally High (except in step 6), counter 463 is normally reset. In step 6, however (the step in which aspiration of a sample occurs) it counts until its Q10 output goes High (about 6 seconds). This is supplied via connector C45 to input E11 of the multiplexer. Counter 465, on the other hand, is not reset but rather provides slower clock pulses to the rest of the circuitry. For example, the Q3 output of counter 465 is supplied via connector C43 to the inputs of multiplexer 427 discussed above. The Q7 output of timer 465 is supplied on a line L27 to single step control circuit 435. The output of timer 461 is also supplied to one input of gate G57. The other input of that gate is connected to connector C49 (see input E7 to the multiplexer), which is High only when the needle is in its "out" position. The output of gate G57 is supplied to one input of gate G55, the other input of which is connector C17, the runline, the output of which enables or inhibits a set of four NAND gates G57 discussed below, which control stepper motors M1 and M2. Motors M1 and M2 are thereby inhibited unless the needle is "out".

Referring back to FIG. 27B, bit 6 of PROM 429B is also connected, via a line L29, to an autostop circuit 467 which includes four NAND gates G59, G61, G63 and G65. More specifically, bit 6 is connected to one input of gate G65. The other inputs to circuit 467 include the runline (connector C17), a signal indicating the presence or absence of a tube at the sampling station (on connector C41), and bit 0 of PROM 429A. These last two inputs are supplied to gate G59. Bit 0 is High only in step 8, which is right before the feed cycle. If a tube is not present during that step, connector C41 is also High, causing the output of gate G59 to go Low. This sets a flip-flop consisting of gates G61 and G63 with the output of gate G61 High. This output is supplied to gate G65. The output of gate G65 remains High until bit 6 of PROM 429B goes High (step 1 of the program), at which point the output of gate G65 goes Low. This Low is supplied via connector C25 to set Load flip-flop FF1 and, via gate G3 (FIG. 25B) and a line L31, to reset Run flip-flop FF2. When the Run flip-flop is reset, the runline is brought Low, which causes the apparatus to stop. Thus, the autostop circuit causes the apparatus to stop at the proper time, i.e., after the feed cycle, if no tube is present at the sampling station.

Bit 7 of PROM 429B is connected to one input of start-up flip-flop 433. The other input is connected to connector C1, the start-up signal. Upon start-up, the signal on connector C1 causes the output of flip-flop 433 to go High. This High is supplied to the E input pin of both PROMs 429A and B. This corresponds to the hexadecimal address 10. Thus, upon start-up the program starts at step 10. If the shafts are in the load position, the program continues to step 11, the only step in which bit 7 of PROM 429B is Low. This Low resets the start-up flip-flop, causing its output to go Low. This removes the High from the E address pin of the PROMs and leaves the program in step 1. If the shafts are not in the load position, the operator must advance the program counter manually by depressing the switch (i.e., moving it from its normal position shown in FIG. 27B to contact the normally open contact) in the single step control section 435. This causes the output of a flip-flop in circuit 435 to go High. When the clock pulse on line L27 also goes High, the output of a NAND gate G67 goes Low. The output of this gate is supplied to gate G23, causing its output to be a series of clock pulses having the same period as those on line L27. These pulses are supplied to the count up input of the program counter. Once the program counter reaches the step at which the apparatus stopped, the apparatus resumes normal operation and performs the operations set forth in the program until both shafts are in the load position with no tube present at the sampling station, at which point the apparatus stops.

As mentioned above, bit 0 of PROM 429A is connected to the autostop circuit. Bit 1 of the same PROM is connected via connector C67 to the reset input of counter 463, thereby providing a delay of about six seconds (in step 6) in the program to provide sufficient time for aspiration of a sample. Bit 2 of PROM 429A controls solenoid valve 235. Bit 2 is connected via a connector C69 to circuit 355 (see FIG. 28C). Bit 3 of PROM 429A is connected via connector C44 to gate 413 (see FIG. 26E) and thereby controls the operation of carriage motor 109.

Bits 4–7 of PROM 429A are connected via lines L31, L33, L35, and L37 to the inputs of NAND gates G57 and control the direction of rotation of shafts S1 and S2. The other inputs to these gates, as described above, are clock pulses from gate G55 in clock 421. The outputs of gates G57 are connected to a pair of counters 469 whose outputs are connected to a pair of PROMs 471 and 473. Bits 4 and 5 of PROM 429A control shaft S1 up and shaft S1 down motion respectively, while bits 6 and 7 control the corresponding motions of shaft S2. As explained in my above-mentioned U.S. patent, the outputs of PROMs 473 and 471 supply the actual signals to stepper motors M1 and M2 to cause them to step up and down as desired.

Circuit 425 (see FIG. 27A) includes an inverter 475 and five light-emitting diodes 477, which visually display to the operator the step of the program the apparatus is executing. The A–E outputs of the program counter are directly connected to inverter 475 so that when a particular step is being executed the inverter provides a ground for the corresponding diodes, causing them to light.

Figure 28E:
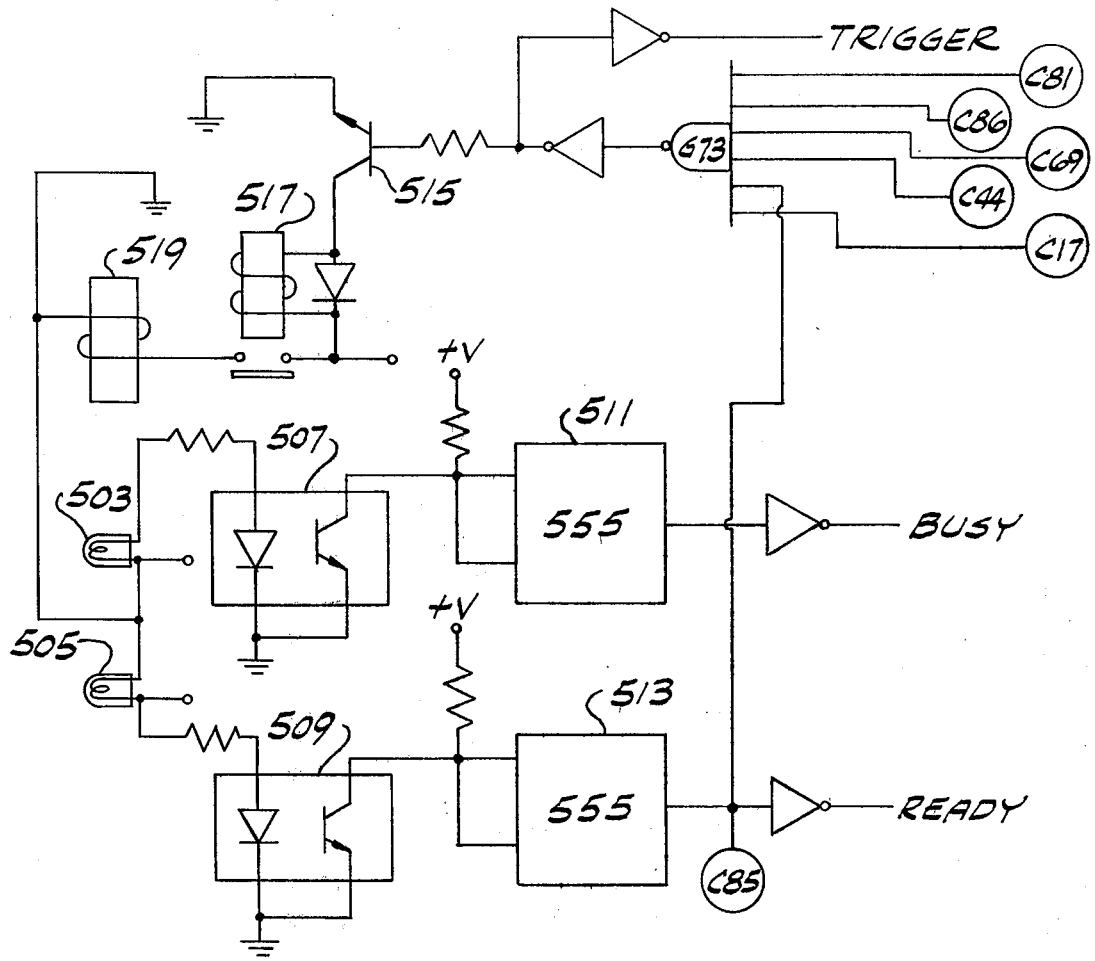

The interface board (see FIGS. 28A–28E) includes circuitry shown on FIG. 28A for controlling pumps P1 and P2. This circuitry includes a flip-flop 479, 481 for each pump (flip-flop 479 being for pump P1 and the other flip-flop being for pump P2), a twelve-stage binary counter 483, 485 for each pump, and a 555 timer 487, 489 for each. Together these components determine the amount of time each pump remains on. This time can be adjusted at the timers. Typical operating times are 15 seconds for pump P1 and 20 seconds for pump P2. During start-up, both flip-flops are reset by the start-up signal on connector C1 (via a logic circuit). During operation, they are set by bit 1 of PROM 429A (connected to a logic circuit via connector C67) and are also set during mixing of the samples (via connector C11 from the Mix flip-flop). The Q outputs of both flip-flops are connected through logic circuits to A.C.

relays 379 which control motors M5 and M6 for pumps P1 and P2 respectively. Manual override switches 491, 493 are provided for each pump. In addition, lid interlock switch 365 is connected to the input circuitry for both pumps so that the pumps will shut down in the event the door is opened during operation of the pumps. In addition, the runline (connector C17) is connected to the interlock switch, to timers 487, 489 and to the logic circuitry for A.C. relays 379. As a result when the interlock switch closes, the runline is pulled Low and when the runline is pulled Low, the timers are stopped as are pumps P1 and P2.

The Q12 output of each counter 483, 485 is connected via an inverter and further logic gates to the reset input of its respective flip-flop, while the clock input of each counter is connected to its associated timer. After the preset number of counts, therefore, counters 483, 485 cause their respective flip-flop to be reset and the associated pumps to stop. The Q outputs of flip-flops 479 and 481 are supplied to the associated counters and, via connectors C75 and C77, to the rest of the circuitry. The Q output of flip-flop 481 is also supplied, via connector C63 to the circuitry shown on FIG. 27A.

The mode control switch (see FIG. 28B) is connected directly to a flip-flop 495 whose Q output is supplied via a connector C81 to the rest of the circuit. In one position, the mode switch sets the flip-flop. In the other it resets it.

FIG. 28C shows circuitry for operating solenoid valves 173 and 235. One input to this circuitry is supplied via a connector C83 from an aspiration flip-flop 497, described below. If this input is High, operation of solenoid valve 173 is inhibited. The other two inputs are supplied, via connectors C53 and C69 from PROM 429B, bit 4 and PROM 429A, bit 2 respectively. Bit 4 controls the operation of valve 173 as follows. When bit 4 is Low, this Low is inverted and supplied to a NAND gate G69. The other input of gate G69 is also High, unless the inhibit signal from the aspiration flip-flop is present, so its output is Low. This Low is inverted and supplied to the base of an NPN transistor which thereupon conducts, providing a path to ground for solenoid 173. The operation of valve 235 is controlled by bit 2 of PROM 429A.

An out-of-synch system (see FIG. 28D) for the apparatus includes a NAND gate G71, an inverter 499 and an NPN transistor 501. The inputs to gate G71 are bit 2, PROM 429A (on connector C69), bit 3, PROM 429A (on connector C44), an inverted signal (on a connector C85) from Coulter counter module 377 indicating that the counter is ready to accept a sample, and a signal from mode flip-flop 495 (on connector C81). At step 7, if all the inputs to gate G71 are High, the Coulter counter is not ready to accept a sample. The output of gate G71 goes Low, the output of inverter 499 goes High, and transistor 501 conducts, pulling the runline, connector C7, Low.

The interface circuitry between apparatus 1 and the Coulter counter, as well as the relevant portions of the counter itself are shown in FIG. 28E. The Coulter counter includes a red lamp 503 which indicates it is not ready to receive a sample, and a green lamp 505 which indicates it is ready. When one of these lamps light, that is sensed by sensors 507, 509 respectively, and the resulting signal is supplied to associated 555 timers 511, 513 configured as Schmidt triggers. The output of the trigger associated with the green lamp is supplied via connector C85 to gate G71 (see FIG. 28D) and to a NAND gate G73 which controls aspiration of a sample into the Coulter counter. The other inputs to gate G73 include the output of the mode control flip-flop (via connector C81), the inverted output of the aspiration flip-flop (via a connector C86), bit 2 of PROM 429A (via connector C69), bit 3 of PROM 429A (via connector C44), and the runline. When these inputs are all High, the output of gate G73 is Low. This Low is inverted and the resulting High is supplied to the base of an NPN transistor 515, which thereupon conducts, closing a relay 517. When relay 517 closes it completes a circuit to a solenoid valve 519, which is part of the circuitry of this invention but which is physically located in the touch bar control module of the Coulter counter, causing the specimen to be drawn into the counter just as if the touch bar had been depressed. The outputs of triggers 511 and 513 as well as the inverted output of gate G73 are inverted again to light the trigger, busy and ready indicators 367 as appropriate.

Aspiration flip-flop 497 (see FIG. 29A) has supplied to its set input the signal from bit 1 of PROM 429A (via connector C67). The manual short sample reset signal (from the short sample switch via connector C21) and the start-up signal (via connector C1) are supplied to its reset input. The Q output of flip-flop 497 is inverted and supplied via connector C83 to the circuitry of FIG. 28, this being the output of the aspiration flip-flop referred to above. The Q output is supplied to a NAND gate G75, the other input of which is bit 1 of PROM 429A (supplied via connector C67). If both these inputs are High, the output of gate G75 is Low. This Low is supplied to a NAND gate G77, causing its output to go High. This High is supplied by connector C15 to decoding circuitry 385 (see FIG. 25B), causing the short sample lamp to light. It is also supplied to the base of an NPN transistor 521, causing it to conduct and pull the runline Low, thereby stopping the apparatus.

Sensor 157 for sensing the presence of blood or the like at a predetermined position in conduit 65 is also shown in FIG. 29A. Besides the sensor unit itself, there is shown a gain control 523, a Cherry Semiconductor Corp. CS 180 type comparator 525, an optocoupler 527, and a 555 timer 529 configured as a trigger circuit. When blood is detected at sensor 157, the output of trigger 529 is supplied via a NAND gate G79 to the clear input of a 74193 type four-bit binary counter 531. The clock input to counter 531 is connected to a 30 Hz source (not shown). Therefore, counter 531 begins counting. If the output of trigger 529 does not change within about ½ second, the carry pin of the counter goes Low. This pin is connected to the reset input of aspiration flip-flop 497, so the flip-flop is reset, which results in the closing of valve 173. If the sample in conduit was not continuous for ½ second, the output of timer 529 does change, resulting in the clearing of counter 531. This ensures that only a continuous flow of sample will reset the aspiration flip-flop. Counter 531 is also connected to an inverter 533 which provides a ground for a light-emitting diode display 535, which indicates the status of counter 531.

Figure 29B:
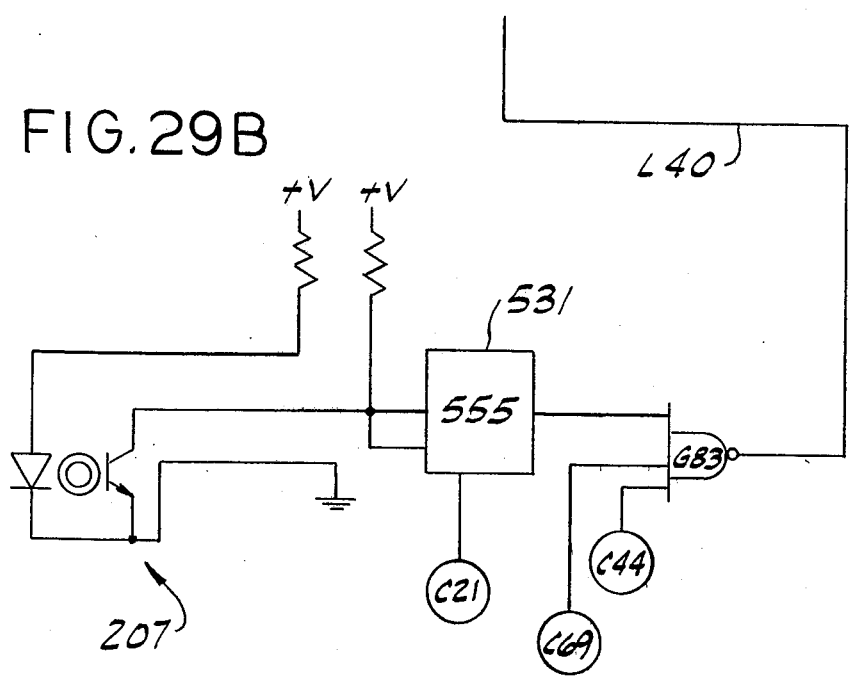
Figure 26D:
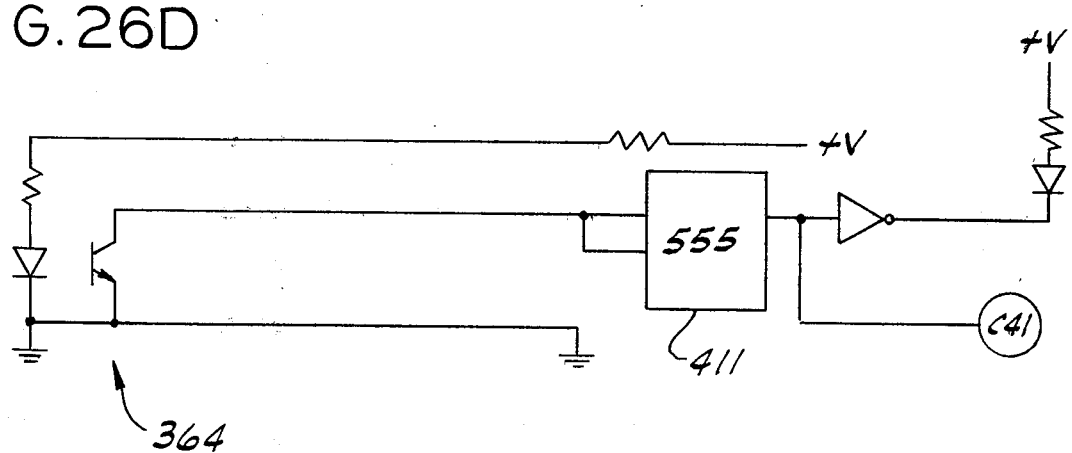

Trailing edge sensor 207 is shown in FIG. 29B. As described above, sensor 207 senses the presence or absence of the sample at a specified point. The sensor is connected to a 555 timer 531 configured as a Schmitt trigger. If a sample is present at sensor 207, the output of trigger 531 is Low; otherwise it is High. This output is supplied to a NAND gate G83, the other inputs of which are from bit 2 of PROM 429A (via connector C69) and from bit 3 of PROM 429A (via connector C44). If a sample is not present at the end of step 6, the output of gate G83 will go Low. This Low is supplied via a line L40 to gate G77, causing the runline to be brought Low, stopping the Sampler. This prevents insufficient sample from entering the Coulter counter. To overrule this, the Short Sample reset button must be depressed during step 7. This supplies a Low on connector C21 to trigger 531, forcing the output of the trigger Low.

The operation of the apparatus is as follows: As described above, when the power is turned on, program counter 431 starts at address 10 (hexadecimal). If shafts S1 and S2 are in the load position, which is the position in which they are adapted to hold containers C horizontal, clock pulses are gated to the E13 input of multiplexer 427, which causes the program counter to be incremented. If not, the operator uses single step control switch 435 to step through the program until the shafts are in the proper position. In step 11 (hexadecimal) of the program, start-up flip-flop 433 is reset and the program counter proceeds to step 1, where it stops with a steady Load light. The apparatus is now ready for tubes to be loaded therein for mixing and/or sampling. In this regard, a plurality of containers C may be loaded between screw shaft sections 25 and additional containers also bulk-loaded via inlet 47 into guideway 33 where the lowermost container in the guideway rests atop the uppermost threads 51 of the screw shaft sections.

Figure 5A:
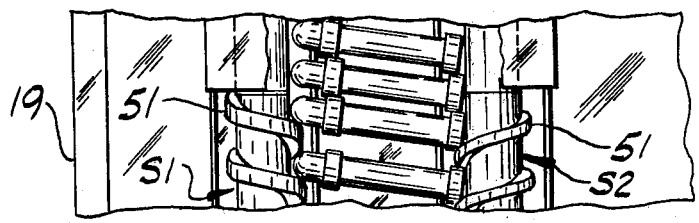
FIGS. 5A–5C are views illustrating how the apparatus mixes the blood in the containers as they move to a sampling station.
Figure 5B:
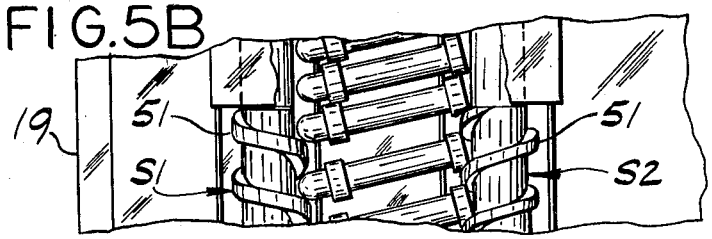
Figure 5C:
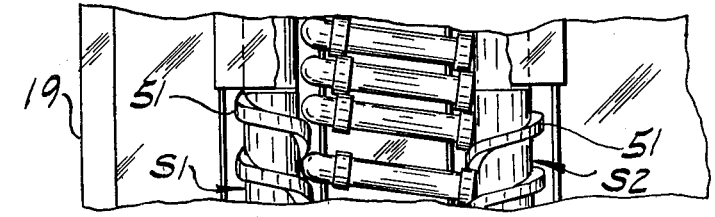

In general, the program can be broken down into several stages. The first stage consists of steps 0 to 3 and is the part of the program, called the mix cycle, in which mixing of the contents of the tubes is accomplished. During the mix cycle, shaft S2 is stationary (because bits 6 and 7 of PROM 429A which control shaft S2 are 0 in those steps). and shaft S1 rotates clockwise and counterclockwise alternately between the shaft S1 high position and shaft S1 low position. This alternate clockwise and counterclockwise rotation of shaft S1 causes the stoppered (right) ends of containers C between screw shaft sections 25 and in guideway 33 to rock up and down and rotate to effect mixing of the contents of the containers (see FIGS. 5A-5C). At the end of step 3, when shaft S1 reaches its high position, program counter 431 is reset to step 0 by counter reset control circuit 449, as is explained above. The program counter is incremented from step 0 to step 1 when shaft S1 is in the load position, from step 1 to step 2 when shaft S1 is in its low position, from step 2 to step 3 when shaft S1 is in its load position, and from step 3 to step 0 when shaft S1 is in its high position.

At the end of step 1 in the mixing cycle, the specimen tube at the sampling station 27 is in the proper tilted position for sampling (see, for example, FIG. 2). During that step, bit 6 of PROM 429B is High, which enables the output of gate G33 in tilt-and-hold circuit 419. If, as described above, the apparatus has completed the desired number of mixing cycles, the output of this gate is Low. This causes the program counter to jump to step 4 or step 8, depending upon whether or not a tube is present at the sampling station. In step 4 another check is made to see if a tube is present at the sampling station. If there is not, the program jumps to step 8. If a tube is present at the sampling station, the program proceeds on to steps 5, 6 and 7, which is called the probe stage or sequence.

Subsequent steps in the operation of sampling apparatus 1 are diagrammatically illustrated in FIGS. 23A-23E.

Figure 23A:
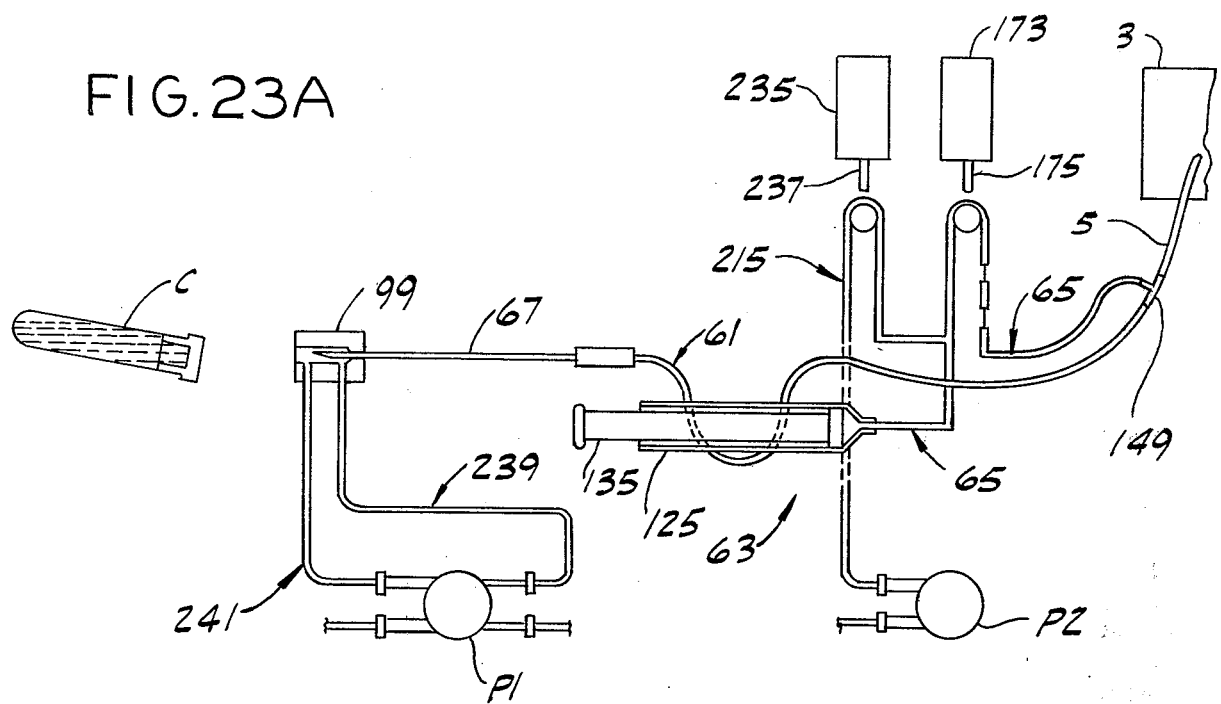
FIGS. 23A–E are diagrammatic views illustrating the sequence of steps involved in obtaining a sample of blood or the like from a container and delivering it to the analyzer, the specimen sample being shown in solid lines and cleaning solution being shown in broken lines.
Figure 23B:
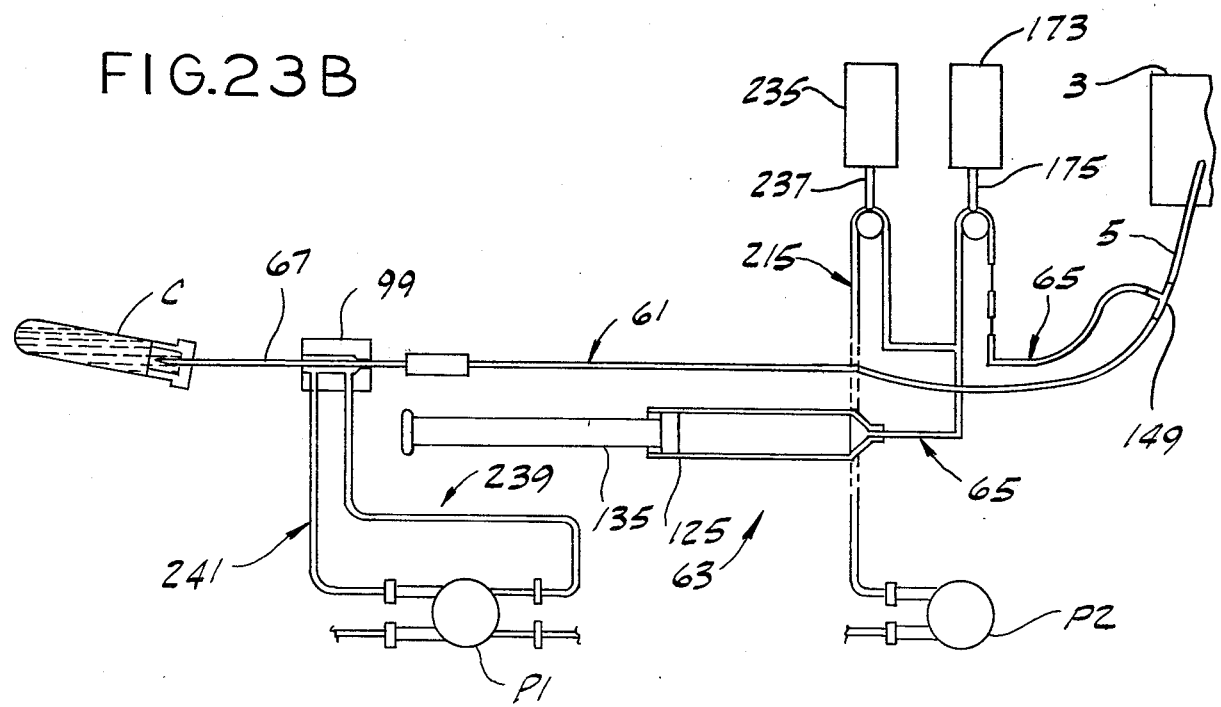
Figure 23C:
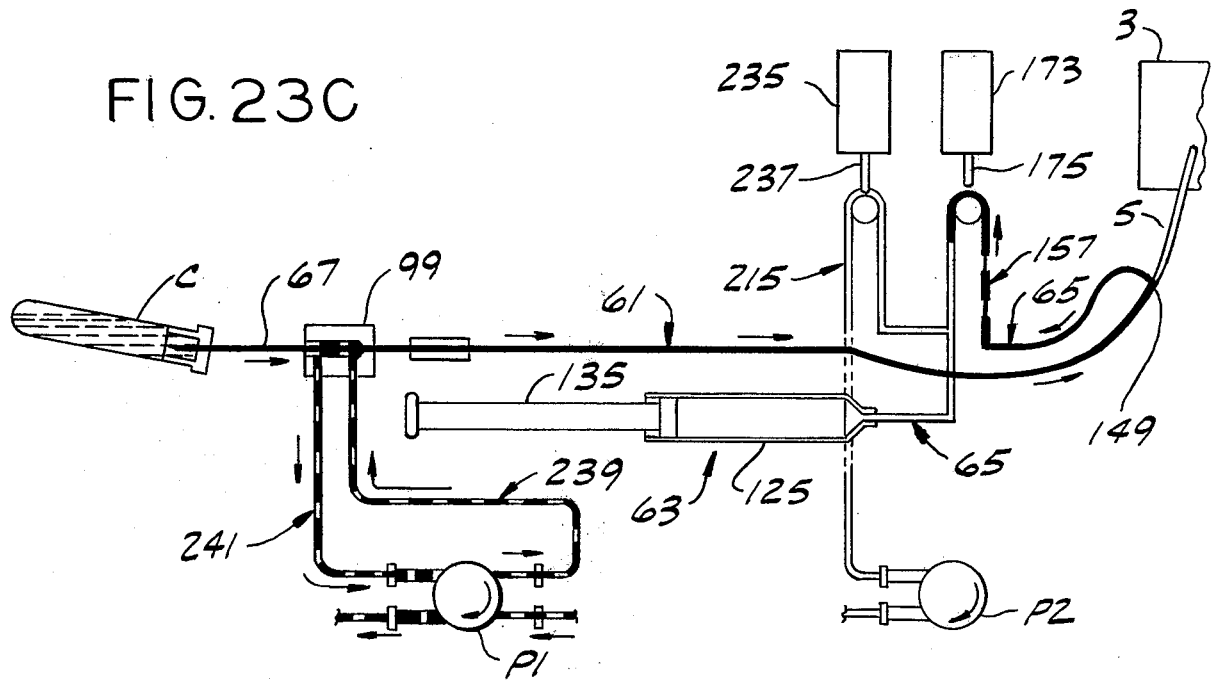
Figure 23D:
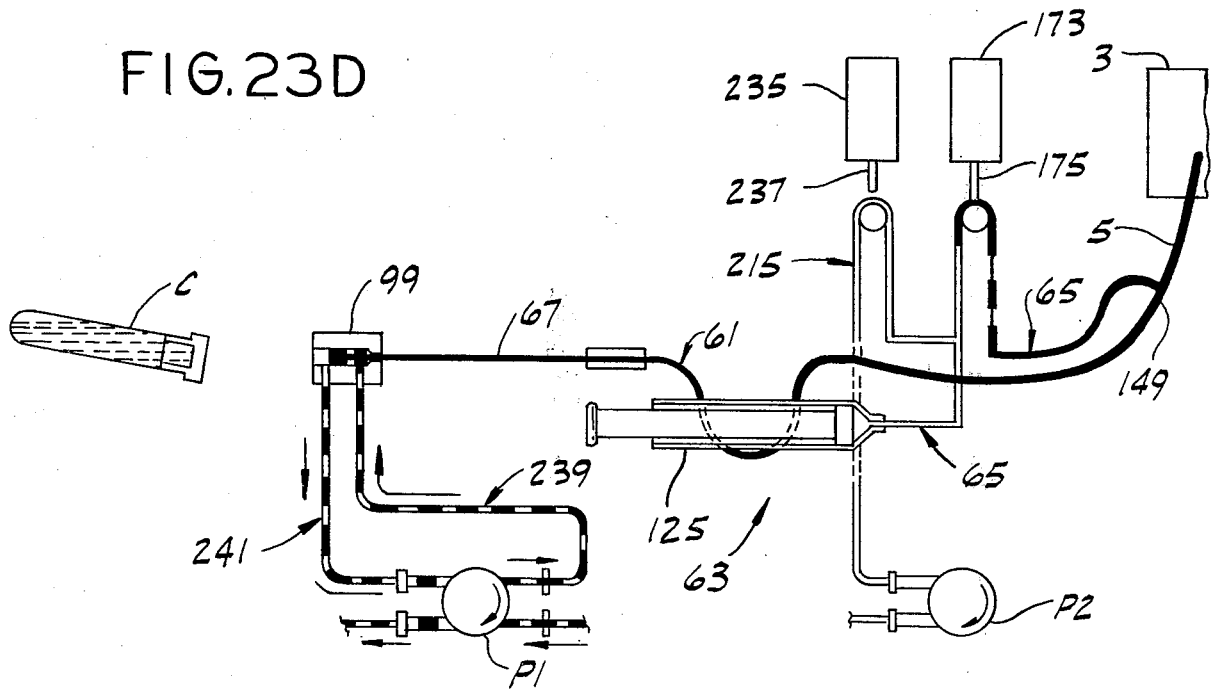

The probe stage is that stage in the program during which the needle 67 and carriage 79 are moved from their retracted position (FIG. 23A) to their extended position (FIG. 23B) in which the needle penetrates the stoppered end of the tube at sampling station 27, a sample is drawn (FIG. 23C), and the needle and carriage are retracted (FIG. 23D). The insertion of the needle into the tube to be sampled occurs in step 5. In this step, bit 3 of PROM 429A is High which, as described above, causes needle carriage drive motor 109 to be energized. In addition, bit 2 of that PROM, which up until this point in the program has been High, goes Low in step 5, thereby energizing valve 235 whereupon plunger 237 moves to its extended position in which it pinches line 225 closed. Bit 4 of PROM 429B, which controls valve 173, also goes Low in this step. This Low is inverted and supplied to gate G69. The other input of this gate is also High, so valve 173 closes as well. Step 5 ends, and motor 109 is stopped, when sensor 123 detects the carriage in the fully extended position. As soon as step 6 starts and the aspiration flip-flop is set, valve 173 opens and the negative pressure generated by the leftward movement of piston 135 in barrel 25 causes a sample to be aspirated from the container at the sampling station. Step 6 is set, by clock 421 and the program, to last about six seconds. As soon as a continuous leading front edge of sample passes sample conductivity sensor 157, the aspiration flip-flop is reset, which causes valve 173 to close. This removes the negative pressure and stops the aspiration of sample from the tube at the sampling station.

Figure 23E:
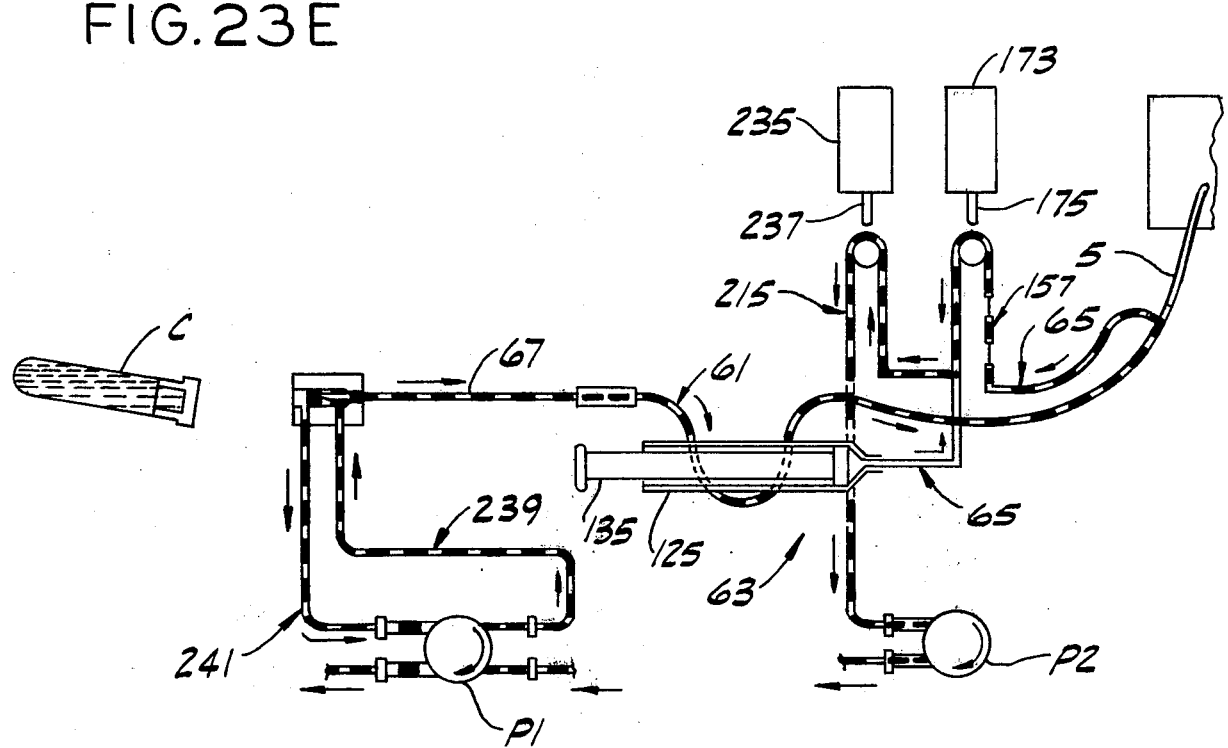

During the next step, step 7, bit 3 of PROM 428A goes High, triggering the motor 109 of carriage drive assembly 107 to move carriage 79 and needle 67 and piston 135 mounted thereon back to their retracted positions (FIG. 23C) As shown in FIG. 23D, valve 235 also opens during step 7 (because bit 2 of the same PROM is High) and analyzer 3 (e.g., a "Coulter" counter) is triggered to aspirate a portion of the sample in conduit means 61 into intake line 5 (FIG. 23E). This later function occurs because in step 7 all the inputs to gate G73 (see FIG. 28E) are High. Thus, gate G73 and the circuits supplying inputs thereto (particularly the aspiration flip-flop and sensor 157) constitute means responsive to the termination of an aspiration period (which may be six seconds long) to trigger the "Coulter" counter to initiate transfer of specimen sample in conduit means 61 through intake line 5 and into the counter. Step 7 lasts about one second. Shortly after the "Coulter" counter is triggered (e.g., 1-2 seconds), it aspirates about one milliliter of the sample. Perastaltic pump P1 is turned on in step 6 or 7, causing cleaning solution to be pumped via supply line 239 into rinsing chamber 99 for washing the outer surface of the needle as it moves back to its retracted position. Pump P2 is also actuated simultaneously with pump P1.

While aspiration by analyzer 3 is taking place, apparatus 1 is going through the feed stage or cycle. During this cycle, steps 8 through F (hexadecimal), shafts S1 and S2 are rotated to dump the sampled container and to bring the next container into position for sampling. If no container is present at the sampling station, the autostop flip-flop, circuit 467 (see FIG. 27B), is set in step 8. In step 9, shaft S2 is rotated to bring the specimen tubes into horizontal position. Both shafts are then simultaneously rotated down to cause the bottom tube between the shafts to be dumped. Then, in step D (hexadecimal), the downward rotation stops and shaft S2 is rotated up until it reaches its load position. The program then continues with the movement of shaft S1 up and down in preparation for sampling the specimen in the next tube. Meanwhile, after step C (hexadecimal), valve 173 is opened (FIG. 23E), enabling pump P2 to draw the cleaning solution in rinse chamber 99 through needle inlet 71, needle passage 69, needle outlet 73, conduit means 61 and 65 and discharge conduit means 215 to flush the system. If aspiration into the Coulter counter takes longer than this, the contents of bit 4 of PROM 429B can be altered to leave valve 173 closed for a slightly longer period.

There are two other functions of apparatus 1 that are relevant to the present invention: the short-sample alarm function and the short-sample restart function. If at the end of step 6 a continuous leading edge of sample has not passed sensor 157, the aspiration flip-flop will not be reset. This causes the runline to be Low, stops the apparatus and turns on the short-sample indicator. The alarm alerts the operator who, after looking to see how much sample has been aspirated from the specimen tube, can select to either let the sample be aspirated into the analyzer 3 by pushing the Short Sample button or, in the case of too little sample being present, can turn the mode switch to OFF LINE and then press the Short Sample button. In this latter case, the apparatus will continue through the program but no trigger signal will be sent to the analyzer, thus preventing aspiration of an insufficient sample. Normal operation is resumed by turning the mode switch back to ON LINE after needle carriage 79 has returned to its fully retracted position.

The short-sample restart function occurs when sample aspiration requires more than six seconds due to highly viscous blood or a partial clot in the conduits or the like. After six seconds, the alarm will occur as before. But as soon as the blood passes conductivity sensor 157 and the delay counter has delayed for about one-half second, the aspiration flip-flop is reset. As a result the runline is no longer pulled Low, the alarm stops, and the apparatus resumes normal operation. Occasional sluggish flow during aspiration will, therefore, not prevent automatic operation of the apparatus. But the operator will be alerted by the alarm to the fact that the sample took longer than six seconds for aspiration. If this occurs frequently, the operator will be alerted to the fact that the aspiration system may contain a small clot or that some other malfunction is gradually occurring.

A further safeguard of the apparatus lies in the trailing edge short sample alarm shown on FIG. 29B. If a sample is not present at sensor 207 after the end of step 6, i.e. after six seconds of aspiration from the specimen tube, it indicates that the conduits do not contain sufficient sample for aspiration into the Coulter counter. As described above, if this occurs the signal on line L40 causes the runline to be pulled Low, stopping the apparatus and sounding the alarm. Thus, even if the leading edge of the sample passed conductivity sensor 157 and the aspiration flip-flop has been reset, the apparatus will stop if the trailing edge of the aspirated sample has passed the trailing edge sensor, which occurs for example when there was too little blood in the specimen tube to fill the conduit. This alarm again prevents insufficient sample from entering the Coulter counter. To overrule this alarm, the Short sample switch must be depressed during step 7.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. Apparatus for obtaining a sample from a specimen of blood or the like in a closed container at a first pressure and for delivering said sample to an analyzer for analysis, said analyzer having intake means for intake of said specimen sample into the analyzer, said apparatus comprising:

means for penetrating said closed container, said means having a passage therein with an inlet for entry of a specimen sample into the passage and an outlet for exit of the sample from the passage, said penetrating means being movable from a retracted position to an extended position in which it penetrates said closed container with said inlet in position for entry of a specimen sample into said passage, and back to said retracted position;

first conduit means connecting the outlet of said passage with said intake means of the analyzer for delivery of a specimen sample to the latter;

means for reducing the pressure in said conduit means to a pressure less than said first pressure when said penetrating means is in said extended position thereby to aspirate a specimen sample from the container into said passage and said conduit means for delivery to the intake means of said analyzer; and means responsive to said aspiration to initiate transfer of said sample from said conduit means into the analyzer, the pressure in said passage and conduit means being at least equal to said first pressure following said aspiration thereby enabling said specimen sample readily to be drawn through said intake means into said analyzer for analysis.

2. Apparatus as set forth in claim 1 further comprising means for moving said penetrating means through an aspiration cycle, said means being operable during said cycle for moving said penetrating means from said retracted to said extended position, said penetrating means being adapted to remain in said extended position for a predetermined interval of time constituting an aspiration period during which said specimen sample is aspirated from said closed container, and for moving said penetrating means from its extended back to its retracted position after termination of said aspiration interval.

3. Apparatus as set forth in claim 2 wherein said means for reducing the pressure comprises an aspirator operable to produce a negative pressure as said penetrating means moves from its retracted to its extended position.

4. Apparatus as set forth in claim 3 wherein said aspirator comprises cylinder means having an opening adjacent one end thereof in communication with said first conduit means, and a piston movable axially in the cylinder means between a retracted position in which it is relatively close to said one end of the cylinder means and an extended position in which it is further away from said one end.

5. Apparatus as set forth in claim 4 wherein said cylinder means comprises a cylindrical barrel.

6. Apparatus as set forth in claim 4 wherein said means for moving the penetrating means through an aspiration cycle comprises carriage means, said piston being mounted on the carriage means for movement therewith from its retracted to its extended position as said penetrating means moves from its retracted to its extended position and for movement from its extended back to its retracted position as said penetrating means moves from its extended back to its retracted position.

7. Apparatus as set forth in claim 6 wherein said carriage means comprises a guide rod, a carriage slidable on the guide rod carrying said penetrating means and piston, and drive means for reciprocating the carriage along the guide rod thereby to move said penetrating means and piston between their respective retracted and extended positions.

8. Apparatus as set forth in claim 6 further comprising second conduit means communicating with said first conduit means and extending from said intake means to the opening at said one end of said cylinder means, and first valve means for closing said second conduit means as the piston and penetrating means move from their retracted to their extended positions, and for opening said second conduit means when the piston and penetrating means reach their extended position thereby to permit aspiration of a specimen sample from said closed container.

9. Apparatus as set forth in claim 8 further comprising sensing means in said second conduit means responsive to the flow of the leading end of an aspirated specimen sample therepast for generating a signal to actuate said first valve means to close said second conduit means.

10. Apparatus as set forth in claim 9 wherein said sensing means is operable to signal an alarm if the leading end of said specimen sample has not reached it at the end of said aspiration period.

11. Apparatus as set forth in claim 8 further comprising discharge conduit means in communication with said second conduit means between said aspirator and said first valve means, and second valve means operable to close said discharge conduit means before said piston and penetrating means move from their retracted to their extended positions and to open said discharge conduit means after termination of said aspiration period and before said piston and penetrating means move from their extended back to their retracted positions.

12. Apparatus as set forth in claim 11 further comprising means for flushing and cleaning said needle passage, said first and second conduit means and said discharge conduit means after completion of said aspiration cycle.

13. Apparatus as set forth in claim 1 wherein one end of said container is puncturable and said penetrating means comprising a hollow needle adapted for penetration through said penetrable end of the container.

14. Apparatus as set forth in claim 13 wherein said inlet comprises an opening in the needle through which a specimen sample may be aspirated into said passage and said first conduit means, said inlet being exposed to the atmosphere when the needle is moved from its extended back to its retracted position following said aspiration period.

15. Apparatus as set forth in claim 13 further comprising means for cleaning the outer surface of said needle when the latter is in its retracted position, said means comprising a rinse chamber, a line for supply of a cleaning solution or the like to said chamber, and a line for drainage of said chamber, said needle being receivable in said rinse chamber when in its retracted position.

16. Apparatus as set forth in claim 14 wherein said cleaning means further comprises a first pump operable as said needle moves to its retracted position for pumping cleaning solution or the like through said supply line into said rinse chamber, the cleaning solution exiting the chamber via said drain line.

17. Apparatus as set forth in claim 16 wherein said first pump is operable for a predetermined time interval after said needle has returned to its retracted position to pump said cleaning solution through said supply line into said rinse chamber, said apparatus further comprising means for flushing and cleaning said needle passage and said first conduit means during said predetermined time interval.

18. Apparatus as set forth in claim 17 wherein said flushing means comprises discharge conduit means communicating with said first conduit means and a second pump operable during said predetermined time interval for pumping cleaning solution from said rinse chamber through said needle passage, said first conduit means and said discharge conduit means for flushing them.

19. Apparatus as set forth in claim 2 further comprising sensing means at a location in said first conduit means responsive to the absence of said specimen sample at said location after the termination of said aspiration period for signalling an alarm.

20. Apparatus as set forth in claim 1 further comprising means for effecting an increase of the pressure in said closed container to a pressure greater than said first pressure thereby to assist in the aspiration of said specimen sample from said closed container.

21. Apparatus as set forth in claim 20 wherein said means for effecting an increase of the pressure in said closed container is operable to increase said pressure prior to aspiration of said sample from said container.

22. Apparatus as set forth in claim 21 wherein said means for effecting an increase of the pressure in said closed container comprises an opening in said first conduit means providing communication between said first conduit means and a source of pressure greater than said first pressure, and valve means movable between a closed position for sealing said opening and an open position for permitting communication between said first conduit means and said pressure source.

23. Apparatus as set forth in claim 22 wherein said valve means is operable to move to its open position when said penetrating means moves to its extended position within said closed container, the interior of the container thereby communicating with said pressure source via said inlet, said passage, said first conduit means and said opening, said valve means then being operable to move to its said closed position for enabling the pressure in said first conduit means to be reduced for aspiration of a specimen sample from the container.

24. Apparatus as set forth in claim 22 wherein said means for effecting an increase of the pressure in said closed container further comprises means for enclosing said first conduit means at said opening, said enclosing means communicating with said pressure source and having a sealing fit with said first conduit means on opposite sides of said opening to form a pressure chamber surrounding said first conduit means and communicating therewith via said opening.

25. Apparatus as set forth in claim 24 wherein said enclosure means comprises a sleeve around said delivery line and plugs in opposite ends of the sleeve for sealing the space around said first conduit means between the latter and the sleeve, said sleeve having an inlet communicating with said pressure source.

26. Apparatus as set forth in claim 24 wherein said enclosure means is of resilient material and said valve means comprises a solenoid valve having a plunger movable from a retracted position to an extended position in which it presses said enclosure means against said first conduit means to seal said opening therein and back to said retracted position in which it permits the enclosure means to spring back away from said opening.

27. A method for obtaining a sample from a specimen of blood or the like contained in a closed container at a first pressure and for delivering said sample to an analyzer for analysis, said analyzer having intake means for intake of said specimen sample into the analyzer, said method comprising:
penetrating said closed container with means connected via conduit means to said intake means, said penetrating means having a passage therein with an inlet for entry of a specimen sample into the passage and an outlet for exit of the sample from the passage into said conduit means;
reducing the pressure in said passage and said conduit means to a pressure less than said first pressure thereby to aspirate a specimen sample from the container into said passage and conduit means for delivery to the intake means of the analyzer;
withdrawing said penetrating means from said container following aspiration of the specimen sample from the container, the pressure in said conduit means then being at least equal to said first pressure; and
initiating transfer of specimen sample from said conduit means into said analyzer.

28. A method as set forth in claim 27 further comprising effecting an increase of the pressure in said conduit means to a second pressure greater than said first pressure following said aspiration.

29. A method as set forth in claim 27 further comprising effecting an increase of the pressure in said closed container to facilitate aspiration of said specimen sample from the container.

30. A method as set forth in claim 29 wherein the increase of said pressure in said closed container is effected prior to reducing the pressure in said passage and conduit means.

31. A method as set forth in claim 30 wherein the increase of the pressure in said closed container is effected by venting the interior of the container to atmosphere.

32. A method as set forth in claim 30 wherein said pressure in said closed container is increased to a pressure greater than atmospheric pressure.

33. A method as set forth in claim 27 further comprising washing said penetrating means after it is withdrawn from said closed container.

34. A method as set forth in claim 29 further comprising flushing said passage and conduit means with a cleaning solution or the like to clean them following said transfer of specimen sample from said conduit means into the analyzer.

35. Apparatus for obtaining samples from specimens of blood or the like contained in closed containers, said apparatus comprising conveyor means, means for feeding a plurality of said containers one after another in a predetermined sequence to said conveyor means, the latter being adapted for moving said containers separately and in said predetermined sequence to a sampling station and for imparting motion to the closed containers while they are moved to the sampling station to obtain a substantially uniform distribution of particles contained therein, and means for penetrating the closed containers when they reach the sampling station to withdraw specimen samples from the containers.

36. Apparatus as set forth in claim 35 wherein said feeding means comprises guide means forming a guideway having an inlet through which a plurality of said containers may be loaded into the guide means in said predetermined sequence, and an outlet, said guide means being adapted to present said containers one at a time at said outlet for removal of the containers from the guideway in said predetermined sequence.

37. Apparatus as set forth in claim 36 wherein the inlet of said guideway is at a higher elevation than said outlet and said containers are adapted to gravitate in the guideway from the inlet to the outlet.

38. Apparatus as set forth in claim 37 wherein said containers are elongate tubes and said apparatus further comprises a pair of vertically disposed substantially parallel shafts spaced apart for receiving said containers therebetween stacked one above another in generally horizontal position, said guide means comprising the upper sections of said shafts and means at opposite sides of said upper shaft sections for retaining the containers in stacked position one above another between the shafts as the containers move in said guideway in said predetermined sequence.

39. Apparatus as set forth in claim 38 wherein said conveyor means comprises the lower sections of said shafts, said lower section being threaded and in the form of feed screws rotatable for the individual removal of said containers from the outlet of said guideway in said predetermined sequence.

40. Apparatus as set forth in claim 35 further comprising an elongate tubular body closed at one end and open at its other end, plug means for closing the open end of the container, said plug means having a diameter greater than that of the said tubular body, and adapter means on the body spaced longitudinally of the body from said plug means for increasing the effective diameter of said body to that of said plug means, said plug means and adapter means of one tube being engageable with the plug means and adapter means of another tube for maintaining the two tubes generally parallel as they are fed to said conveyor means.

41. A closed container as set forth in claim 40 wherein said adapter means comprises a sleeve around said tubular body.

42. Apparatus as set forth in claim 41 wherein said sleeve is removably fitted around said tubular body.

43. Apparatus for mixing and then analyzing samples of blood specimens or the like contained in a series of closed containers at a first pressure less than atmospheric, comprising:

means for mixing said blood specimens in the closed containers without opening the containers and for delivering the closed containers to a sampling station;

means for penetrating a closed container at the sampling station thereby to permit aspiration of a specimen sample from the container;

means in communication with said penetrating means for analyzing said blood specimens, said analyzing means being capable of generating a second pressure less than atmospheric but not substantially less than said first pressure; and passage means associated with said penetrating means, said passage means being adapted for communication at one end with the interior of said closed container when said penetrating means has penetrated the container and at its other end with a source of pressure greater than said first and second pressures whereby a pressure increase is adapted to be effected in said closed container when said penetrating means has penetrated the container for aspiration of a blood specimen from the container to said analyzing means for analysis.

* * * * *